(12) United States Patent
Sano et al.

(10) Patent No.: US 10,732,302 B2
(45) Date of Patent: Aug. 4, 2020

(54) RADIATION GRATING DETECTOR AND X-RAY INSPECTION APPARATUS

(71) Applicant: Shimadzu Corporation, Kyoto (JP)

(72) Inventors: Satoshi Sano, Kyoto (JP); Junichi Ohi, Kyoto (JP)

(73) Assignee: Shimadzu Corporation, Kyoto-shi, Kyoto (JP)

( * ) Notice: Subject to any disclaimer, the term of this patent is extended or adjusted under 35 U.S.C. 154(b) by 178 days.

(21) Appl. No.: 15/922,223

(22) Filed: Mar. 15, 2018

(65) Prior Publication Data

US 2018/0267175 A1 Sep. 20, 2018

(30) Foreign Application Priority Data

Mar. 15, 2017 (JP) .................... 2017-050226

(51) Int. Cl.
  *G01T 1/20* (2006.01)
  *A61B 6/00* (2006.01)
  *G01N 23/046* (2018.01)
  *G01N 23/20* (2018.01)

(52) U.S. Cl.
  CPC .......... *G01T 1/2002* (2013.01); *A61B 6/4241* (2013.01); *A61B 6/4291* (2013.01); *A61B 6/484* (2013.01); *G01N 23/046* (2013.01); *G01N 23/20075* (2013.01); *G01T 1/2018* (2013.01); *G01N 2223/419* (2013.01)

(58) Field of Classification Search
  CPC ... G01T 1/2002; G01T 1/2018; G01N 23/046; G01N 23/20075; G01N 2223/419; A61B 6/4241; A61B 6/4291; A61B 6/484

USPC .......................................... 378/6, 62, 37, 70
See application file for complete search history.

(56) References Cited

U.S. PATENT DOCUMENTS

| | | | | |
|---|---|---|---|---|
| 5,812,629 A * | 9/1998 | Clauser | ................. | A61B 6/032 378/37 |
| 7,746,981 B2 * | 6/2010 | Takahashi | ............ | G01T 1/2928 250/370.11 |
| 8,280,000 B2 * | 10/2012 | Takahashi | .............. | A61B 6/484 378/62 |
| 8,632,247 B2 * | 1/2014 | Ishii | ........................ | A61B 6/00 378/207 |
| 8,718,228 B2 * | 5/2014 | Nakamura | ............... | A61B 6/06 378/149 |
| 8,995,615 B2 * | 3/2015 | Yamaguchi | ........... | G01N 23/02 378/147 |
| 10,153,061 B2 * | 12/2018 | Yokoyama | .......... | G02B 5/1838 |
| 2002/0001088 A1 * | 1/2002 | Wegmann | ................. | G01J 9/02 356/521 |
| 2005/0190882 A1 * | 9/2005 | McGuire | ................ | H01J 35/06 378/88 |
| 2007/0183560 A1 * | 8/2007 | Popescu | ................. | A61B 6/032 378/5 |
| 2007/0183562 A1 * | 8/2007 | Popescu | ................. | A61B 6/032 378/19 |

(Continued)

FOREIGN PATENT DOCUMENTS

JP  2012-127685 A  7/2012

*Primary Examiner* — Blake C Riddick
(74) *Attorney, Agent, or Firm* — Muir Patent Law, PLLC

(57) ABSTRACT

The radiation grating detector includes a grating portion constituting at least a second grating among a first grating, the second grating, and a third grating, and a detection portion configured to detect an incident radiation transmitted through the grating portion.

13 Claims, 9 Drawing Sheets

[First Embodiment]

(56) References Cited

U.S. PATENT DOCUMENTS

| | | | |
|---|---|---|---|
| 2007/0183579 A1* | 8/2007 | Baumann | A61B 6/484 378/145 |
| 2007/0183580 A1* | 8/2007 | Popescu | A61B 6/00 378/145 |
| 2009/0128830 A1* | 5/2009 | Kottler | G01B 15/025 356/521 |
| 2010/0027739 A1* | 2/2010 | Lanza | G02B 27/52 378/37 |
| 2010/0074395 A1* | 3/2010 | Popescu | A61B 6/06 378/16 |
| 2010/0220834 A1* | 9/2010 | Heismann | A61B 6/032 378/19 |
| 2010/0246764 A1* | 9/2010 | Itoh | G21K 1/025 378/62 |
| 2010/0278297 A1* | 11/2010 | Borner | A61B 6/032 378/7 |
| 2010/0327175 A1* | 12/2010 | Nesterets | G01N 23/04 250/393 |
| 2011/0085639 A1* | 4/2011 | Nakamura | G21K 1/06 378/62 |
| 2011/0164724 A1* | 7/2011 | Ohta | A61B 6/06 378/62 |
| 2011/0243300 A1* | 10/2011 | Kaneko | A61B 6/06 378/36 |
| 2011/0261924 A1* | 10/2011 | Bredno | A61B 6/032 378/9 |
| 2012/0002785 A1* | 1/2012 | Kaneko | G21K 1/067 378/62 |
| 2012/0008747 A1* | 1/2012 | Roessl | A61B 6/484 378/87 |
| 2012/0033785 A1* | 2/2012 | Michel | G01N 23/20075 378/21 |
| 2012/0057677 A1* | 3/2012 | Vogtmeier | G02B 5/1857 378/85 |
| 2012/0099702 A1* | 4/2012 | Engel | A61B 6/00 378/62 |
| 2012/0099705 A1* | 4/2012 | Murakoshi | A61B 6/4291 378/85 |
| 2012/0106705 A1* | 5/2012 | Mikami | A61B 6/4233 378/70 |
| 2012/0114098 A1* | 5/2012 | Mikami | A61B 6/4233 378/62 |
| 2012/0140882 A1* | 6/2012 | Iwakiri | A61B 6/4233 378/62 |
| 2012/0140883 A1* | 6/2012 | Iwakiri | A61B 6/4233 378/62 |
| 2012/0140884 A1* | 6/2012 | Iwakiri | A61B 6/4233 378/62 |
| 2012/0140885 A1* | 6/2012 | Iwakiri | A61B 6/06 378/62 |
| 2012/0140886 A1* | 6/2012 | Murakoshi | A61B 6/06 378/62 |
| 2012/0145912 A1* | 6/2012 | Iwakiri | A61B 6/06 250/370.08 |
| 2012/0153177 A1* | 6/2012 | Iwakiri | A61B 6/4291 250/370.09 |
| 2012/0155610 A1* | 6/2012 | Murakoshi | A61B 6/4291 378/62 |
| 2012/0163554 A1* | 6/2012 | Tada | A61B 6/4035 378/154 |
| 2012/0236985 A1* | 9/2012 | Schusser | G21K 1/06 378/16 |
| 2012/0250972 A1* | 10/2012 | Tada | A61B 6/4291 382/132 |
| 2012/0288056 A1* | 11/2012 | Murakoshi | A61B 6/4233 378/37 |
| 2013/0010926 A1* | 1/2013 | Tada | A61B 6/06 378/62 |
| 2013/0028378 A1* | 1/2013 | Stutman | G01N 23/04 378/62 |
| 2013/0201198 A1* | 8/2013 | Nagatsuka | A61B 6/463 345/581 |
| 2013/0202081 A1* | 8/2013 | Rossl | G21K 1/06 378/36 |
| 2013/0208864 A1* | 8/2013 | Rossl | A61B 6/484 378/62 |
| 2013/0259194 A1* | 10/2013 | Yip | A61B 6/502 378/37 |
| 2013/0308750 A1* | 11/2013 | Ishii | A61B 6/4233 378/36 |
| 2014/0105353 A1* | 4/2014 | Pfeiffer | G01N 23/046 378/19 |
| 2014/0126690 A1* | 5/2014 | Yamaguchi | A61B 6/484 378/36 |
| 2014/0177789 A1* | 6/2014 | Baturin | A61B 6/484 378/35 |
| 2014/0185746 A1* | 7/2014 | Baturin | A61B 6/484 378/36 |
| 2014/0185752 A1* | 7/2014 | Lu | A61B 6/4035 378/53 |
| 2014/0286477 A1* | 9/2014 | Ishii | G01N 23/04 378/62 |
| 2014/0334604 A1* | 11/2014 | Teshima | G21K 1/025 378/62 |
| 2015/0055743 A1* | 2/2015 | Vedantham | G01N 23/04 378/36 |
| 2015/0182178 A1* | 7/2015 | Baturin | G01N 23/20075 378/36 |
| 2015/0235725 A1* | 8/2015 | Makifuchi | G21K 1/067 378/87 |
| 2015/0243397 A1* | 8/2015 | Yun | G01N 23/20075 378/36 |
| 2015/0248943 A1* | 9/2015 | Handa | A61B 6/4208 378/62 |
| 2015/0294749 A1* | 10/2015 | Gorelick | A61B 6/4291 378/36 |
| 2016/0064109 A1* | 3/2016 | Yamaguchi | G01N 23/20075 378/36 |
| 2016/0252470 A1* | 9/2016 | Momose | G01N 23/20075 378/36 |
| 2016/0349197 A1* | 12/2016 | Kitamura | G01N 23/20008 |
| 2017/0156686 A1* | 6/2017 | Koehler | A61B 6/06 |
| 2018/0356355 A1* | 12/2018 | Momose | A61B 6/00 |
| 2019/0159742 A1* | 5/2019 | Behling | A61B 6/4007 |

\* cited by examiner

[First Embodiment]

[Second Embodiment]

[Third Embodiment]

[Fourth Embodiment]

[Modified Embodiments]
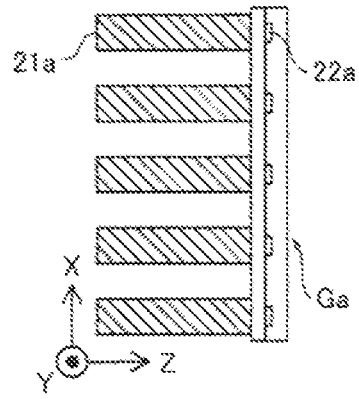
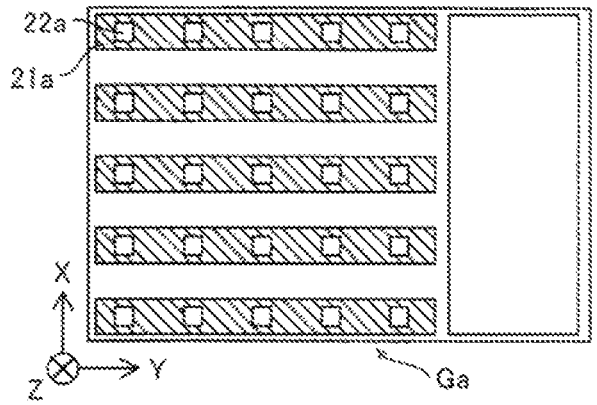
FIG. 8A  FIG. 8B
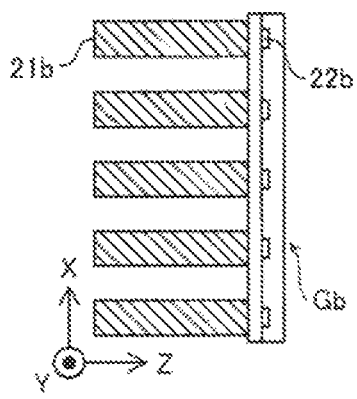
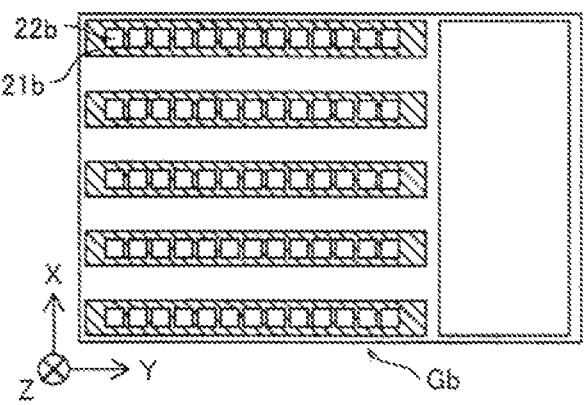
FIG. 8C  FIG. 8D

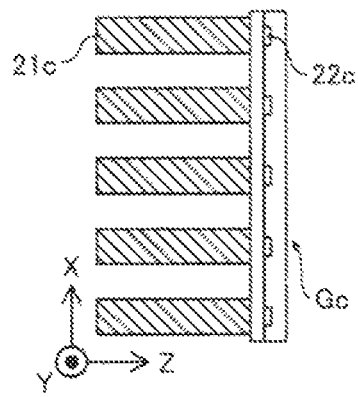 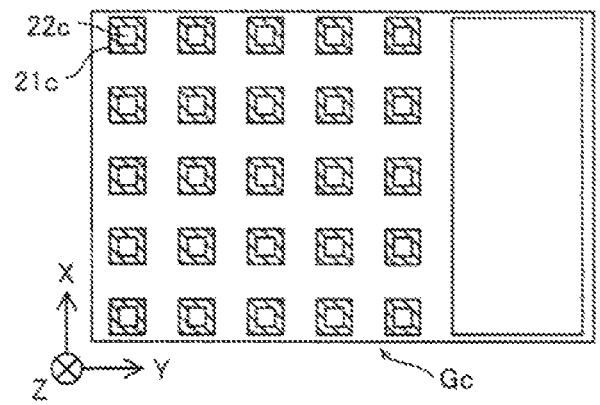
FIG. 8E  FIG. 8F
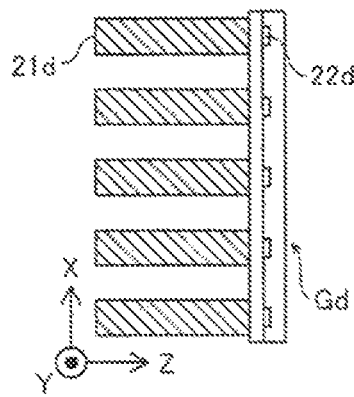 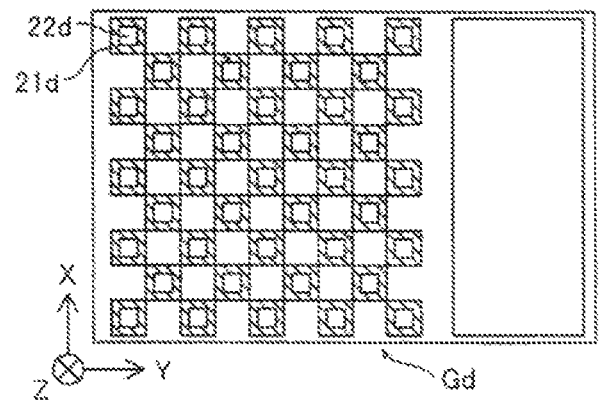
FIG. 8G  FIG. 8H

RADIATION GRATING DETECTOR AND X-RAY INSPECTION APPARATUS

CROSS-REFERENCE TO RELATED APPLICATIONS

The present application claims priority to Japanese Patent Application No. 2017-050226, entitled "RADIATION GRATING DETECTOR AND INSPECTION APPARATUS", filed on Mar. 15, 2017 and invented by Satoshi Sano and Jyunich Ohi, the contents of which are incorporated herein by reference in their entirety.

BACKGROUND OF THE INVENTION

Field of the Invention

The present invention relates to a radiation grating detector and an X-ray inspection apparatus, and more particularly to a radiation grating detector and an X-ray inspection apparatus provided with a grating portion for image-capturing a phase of an X-ray.

Description of Background Art

Conventionally, an X-ray inspection apparatus provided with a grating portion for image-capturing a phase of an X-ray is known. Such an X-ray inspection apparatus is disclosed in, for example, Japanese Unexamined Patent Application Publication No. 2012-127685.

Further, Japanese Unexamined Patent Application Publication No. 2012-127685 discloses an X-ray image capturing apparatus (X-ray inspection apparatus) equipped with an X-ray source (X-ray irradiation portion), a multi-slit (first grating), a first diffraction grating (second grating), a second diffraction grating (third grating), and an X-ray image detector (transmitted X-ray detection portion). Further, it discloses a first silicon layer and a metal grating in which a plurality of second silicon portions linearly extending in one direction and a plurality of metal portions (grating portions) are formed on the first silicon layer, which are arranged alternately in parallel with each other. It is configured such that the second silicon portion (the portion having no grating portion) of the metal grating functions to transmit an X-ray and the metal portion (grating portion) of the metal grating functions to absorb an X-ray. The multi-slit, the first diffraction grating, and the second diffraction grating are constituted by the metal grating.

Specifically, an X-ray is irradiated from an X-ray source toward the multi-slit (first grating) that allows transmission of only the X-ray aligned in phase from the X-ray source and generates a Lau effect of making each transmitting portion of the grating a plurality of light sources (multiple light source, multi light source) aligned in phase. Then, the (phase-aligned) X-ray transmitted through the multi-slit and made into multi-light sources transmits through the subject and then is irradiated to the first diffraction grating. The irradiated X-ray generates a Talbot effect that the X-ray transmitted through the first diffraction grating (second grating) generates light and dark fringes of the X-ray which is a grating image reflecting the form of the first diffraction grating (which becomes similar to the first grating in shape) at a specific distance and forms a Talbot image (self-image of the grating image). Then, the Talbot image is affected by the second diffraction grating (third grating) provided at the position where the Talbot image is generated to form image contrast of a moire fringe. This image contrast is detected by an X-ray image detector. That is, the X-ray image capturing apparatus (X-ray inspection apparatus) of Japanese Unexamined Patent Application Publication No. 2012-127685 is configured to operate as a Talbot-Lau interferometer.

However, in the X-ray image capturing apparatus (X-ray inspection apparatus) described in Japanese Unexamined Patent Application Publication No. 2012-127685, X-ray absorption (loss) occurs in the metal portion (grating portion) of each grating (the multi-slit (the first grating), the first diffraction grating (the second grating), and the second diffraction grating (the third grating)). Therefore, there is a problem that the absorbed X-ray becomes an useless X-ray that is not used for capturing an X-ray image.

SUMMARY OF THE INVENTION

The present invention was made to solve the aforementioned problems, and an object of the present invention is to provide a radiation grating detector and an X-ray inspection apparatus capable of effectively utilizing radiation (X-ray) irradiated to a grating portion.

In order to attain the aforementioned object, the radiation grating detector according to the first aspect of the present invention is a radiation grating detector for use in an X-ray inspection apparatus including at least a second grating among a first grating configured to obtain coherence by making incident radiation in a multi-point light source radiation, the second grating configured to generate a grating image of the incident radiation, and a third grating configured to absorb the radiation to shield the radiation at a position where the grating image is generated, and is configured to includes a grating portion configuring the at least the second grating among the first grating, the second grating, and the third grating and forming a non-opening portion other than an opening portion through which the radiation transmits, and a detection portion provided at the non-opening portion to detect the incident radiation transmitted through the grating portion.

In the radiation grating detector according to the first aspect of the present invention, as described above, it is configured to include a grating portion constituting at least a second grating that generates a grating image of the incident radiation among a first grating, the second grating, and a third grating and a detection portion provided at the non-opening portion and configured to detect incident radiation transmitted through the grating portion.

With this, unlike conventional apparatuses, the radiation transmitted through the non-opening portion (grating portion) is image-captured by the detection portion. For this reason, it is possible to utilize the radiation incident on the non-opening portion which was conventionally uselessly irradiated. In other words, it is possible to effectively utilize the X-ray irradiated to the grating portion. For example, when the detection portion of the present invention is provided at the first grating for aligning the phase of the incident radiation, fluctuations of the irradiation intensity of the X-ray can be detected. Further, when the detection portion of the present invention is provided at the second grating for generating a grating image of the incident radiation, an absorption image with less edge blurring (blurring at the end of the image-captured subject) can be obtained. Further, when the detection portion of the present invention is provided at the third grating that absorbs the radiation to shield the radiation at a position where a grating image is generated, a phase image can be obtained directly at the third grating.

In the present invention, it is assumed that the "radiation image" corresponds to any one or more of an absorption image that represents the absorption (luminance value) of the radiation at each pixel position, a phase image that represents the phase-contrast of the radiation at each pixel position, and a dark field image that represents a difference of clarity (contrast) at the position of each pixel.

In the radiation grating detector according to the first aspect of the present invention, it is preferably configured such that the detection portion includes a plurality of detection elements which corresponds to each pixel and directly or indirectly detects the radiation incident on the non-opening portion to output an electric signal.

With such a configuration, it becomes possible to easily acquire a radiation image not only based on the radiation transmitted through the opening portion but also based on the radiation corresponding to each pixel detected by a plurality of detection elements constituting the detection portion.

In this case, it is preferably configured such that the detection portion further includes a scintillator that converts the incident radiation into light having a frequency lower than a frequency of the radiation, and the detection element is configured by a photoelectric conversion element that detects the light having a low frequency converted by the scintillator and outputs an electric signal.

With this configuration, the radiation having a high frequency which is strong in transmission force and difficult in directly detection can be converted to low frequency light by the scintillator and the converted light can be detected by the photoelectric conversion element. For this reason, it becomes possible to easily detect radiation incident on the position of the grating portion (non-opening portion).

In the radiation grating detector in which the detection portion includes the scintillator, it is preferably configured such that the grating portion functions as an absorption grating that absorbs the incident radiation to prevent transmission of the incident radiation to configure the first grating, the second grating, or the third grating by increasing a thickness of the scintillator with respect to an incident direction of the radiation, and functions as a phase grating that changes a phase of the incident radiation to configure the second grating by reducing the thickness of the scintillator with respect to the incident direction of the radiation With this configuration, it can be easily made to function as an absorption grating or a phase grating simply by changing the thickness of the scintillator with respect to the incident direction of the radiation.

In the radiation grating detector in which the detection portion includes the scintillator, it is preferably configured to further include a transparent substrate provided with the scintillator and configured to allow transmission of the radiation, wherein the transparent substrate is detachably attached to one of element substrates together with the scintillator, the one of element substrates being provided with the photoelectric conversion element.

With this configuration, when the scintillator is attached to the element substrate together with the transparent substrate, it can be made to function as a radiation grating detector that performs absorption (or phase modulation of the radiation) of the radiation at the non-opening portion with respect to the incident radiation and performs image-capturing using the detection portion. Further, when the scintillator is removed from the element substrate together with the transparent substrate, it can be made to function as a normal radiation image capturing apparatus for detecting radiation incident on the position of the grating detection portion.

In the radiation grating detector in which the detection portion includes a plurality of detection elements, it is preferably configured such the detection element is composed of a semiconductor detection element including a semiconductor conversion film that converts the incident radiation into an electric current and an electrode that outputs a current signal converted by the semiconductor conversion film.

With this configuration, it becomes possible to easily detect the radiation incident at the position of the grating portion since radiation which is strong in permeability and difficult to directly detect can be converted to electrons (holes) by the semiconductor conversion film and a current signal generated by a voltage applied between electrodes based on the converted electrons (holes) with the electrode (the semiconductor detection element).

In this case, it is preferably configured such that the semiconductor conversion film is made of a heavy element or the electrode is made to be thick so as to function as an absorption grating that absorbs the incident radiation to prevent transmission of the radiation and configures the first grating, the second grating, or the third grating, and the semiconductor conversion film is made of a light element or the electrode is made to be thin so as to function as a phase grating that changes a phase of the incident radiation and configures the second grating.

In order to achieve the aforementioned object, an X-ray inspection apparatus according to the second aspect of the present invention includes an X-ray irradiation portion configured to irradiate an X-ray to a subject; at least a second grating among a first grating configured to align phases of an incident X ray, the second grating configured to generate a grating image of the incident X ray, and a third grating configured to absorb the X ray at a position where the grating image is generated and shield the X-ray; and a transmitted X-ray detection portion configured to detect the X-ray transmitted through the first grating, the subject, the second grating, and the third grating, wherein the first grating, the second grating, and the third grating configure at least the second grating among the first grating, the second grating, and the third grating, and include a grating portion forming a non-opening portion other than an opening portion through which the X-ray transmits and a grating detection portion provided at the non-opening portion to detect the incident X-ray transmitted through the grating portion.

In the X-ray inspection apparatus according to the second aspect of the present invention, as described above, it configures at least the second grating for generating the grating image of the incident radiation among the first grating, the second grating, and the third grating, and also configures to include a grating portion that forms a non-opening portion other than the opening portion through which the X-ray transmits and a detection portion provided at the non-opening portion and configured to detect the incident radiation transmitted through the grating portion.

As a result, the radiation transmitted through the non-opening portion (grating portion) is image-captured by the detection portion, and therefore it becomes possible to utilize the radiation incident on the non-opening portion which was conventionally uselessly irradiated because it was absorbed in each grating portion without reaching the transmitted X-ray detection portion. That is, it is possible to provide an X-ray inspection apparatus capable of performing an inspection of a subject by an X-ray by effectively utilizing the X-ray irradiated to the grating portion. For example, when the detection portion of the present invention is provided at the first grating for aligning the phase of the incident radiation, fluctuations of the irradiation intensity of the X-ray can be detected. Further, when the detection portion of the present invention is provided at the second grating for generating a grating image of the incident radiation, the X-ray immediately after transmitted through the subject can be detected with the second grating. Therefore, an absorption image with less edge blurring (blurring at the end of the image-captured subject) can be obtained.

Further, when the detection portion of the present invention is provided at the third grating that absorbs the radiation to shield the radiation at a position where a grating image is generated, a phase image can be obtained directly at the third grating provided at a position where a grating image is generated. It is also possible to effectively utilize the X-ray that transmitted through the subject to image-capture the subject with the first grating and/or the second grating. Therefore, unlike the case of providing only the transmitted X-ray detection portion for image-capturing the X-ray after the absorption (loss) of the X-ray by the first grating and/or the second grating has occurred, it is possible to provide an X-ray inspection apparatus capable of reducing the total amount of X-ray to be irradiated to the subject in order to obtain an X-ray image with a necessary sensitivity. As a result, in the X-ray inspection apparatus of the present invention, when the subject is a living body, the exposure dose of the subject can be reduced (and the image-capturing time can be shortened). Further, in the X-ray inspection apparatus of the present invention, when the subject is a non-living body, the image-capturing time of the subject can be shortened.

In the present invention, it is defined such that an X-ray image corresponds to one or more of the absorption image that represents the absorption (luminance value) of the X-ray at each pixel position, the differential phase image (or phase image) that represents the phase-contrast of the X-ray at each pixel position, and the dark field image that represents the difference in contrast of the X-ray at the position of each pixel.

In the X-ray inspection apparatus according to the second aspect of the present invention, it is preferably configured such that the grating detection portion is provided at the second grating configured to generate the grating image of the incident X-rays and is configured to detect the X-ray transmitted through the subject placed in front of the second grating.

With this configuration, since the X-ray transmitted through the subject is image-captured by the grating detection portion provided in the second grating provided relatively close to the X-ray irradiation portion, it is possible to acquire a high definition X-ray image which is relatively few in the edge blurring of the subject and relatively small in the magnification ratio of the subject. Further, since the X-ray is image-captured before occurrence of X-ray absorption (loss) by the element substrate of the second grating and the third grating, it is possible to acquire an X-ray image including a soft X-ray (X-ray with relatively low energy). In particular, in cases where the first grating is not on the path of the X-ray involved in image-capturing, X-ray absorption by the first grating does not occur, and therefore an X-ray image including a soft X-ray can be effectively acquired.

In the X-ray inspection apparatus according to the second aspect of the present invention, it is preferably configured such that a temporal fluctuation of intensity of the X-ray irradiated by the X-ray irradiation portion and detected by the grating detection portion provided in at least one of the first grating, the second grating, and the third grating is obtained, and a correction is made so that luminance of the X-ray image acquired at different times becomes constant based on the obtained temporal fluctuation of the intensity.

With this, even in cases where the intensity of the X-ray irradiated by the X-ray irradiation portion becomes unstable and the luminance of the captured X-ray image fluctuates, it is possible to easily correct the luminance of the X-ray image based on the temporal fluctuation of the intensity of the X-ray irradiated by the acquired X-ray irradiation portion.

In the X-ray inspection apparatus according to the second aspect of the present invention, it is preferably configured such that the first grating, the second grating, and the third grating are configured to be movable relative to each other, it is configured to acquire a positional fluctuation of at least one of the first grating, the second grating, and the third grating based on a change of intensity of the X-ray transmitted through the subject S detected by the grating detection portion provided at at least one of the second grating that generates the grating image of the incident X-ray and the third grating that absorbs the X-ray at a position where the grating image is generated to shield the X-ray and relatively move the first grating, the second grating, and the third grating to correct the positional fluctuation.

With this, even in cases where at least one of the positions of the first grating, the second grating, and the third grating fluctuates due to any external factor (for example, thermal fluctuation), it is possible to capture a desired X-ray image by correcting at least one of positions of the first grating, the second grating, and the third grating.

In the X-ray inspection apparatus according to the second aspect of the present invention, it is preferable that it is configured to acquire an X-ray image in which resolution is complimented based on a combination of at least two or more X-ray images different in resolution among a first X-ray image captured by the grating detection portion provided in the second grating that generates the grating image of the incident X-ray, a second X-ray image captured by the grating detection portion provided in the third grating that absorbs the X-ray to shield the X-ray at a position where a grating image is generated, and a third X-ray image captured by the transmitted X-ray detection portion.

With this configuration, even in cases where the resolution of each of the first X-ray image, the second X-ray image, and the third X-ray image is relatively low, by combining at least two of these X-ray images, it is possible to acquire an X-ray image relatively high in resolution.

In the X-ray inspection apparatus according to the second aspect of the present invention, it is preferable that it is configured to acquire an X-ray image in which a composition of the subject is reflected based on a combination of at least two or more X-ray images captured by the X-ray different in energy among a first X-ray image captured by the grating detection portion provided at the second grating for generating the grating image of the incident X-ray, a second X-ray image captured by the grating detection portion provided at the third grating that absorbs the X-ray to shield the X-ray at a position where a grating image is generated, and a third X-ray image captured by the transmitted X-ray detection portion.

With this, even in cases where each of the first X-ray image, the second X-ray image, and the third X-ray image does not reflect the composition of the subject S, by combining at least two of these X-ray images, it is possible to acquire an X-ray image reflecting the composition of the subject S.

In this case, it is preferable that the grating detection portion includes: a scintillator provided at at least one of the second grating that generates the grating image of the incident X-ray and the third grating that absorbs the X-ray to shield the X-ray at a position where the grating image is generated and configured to convert the incident X-ray into light having a frequency lower than a frequency of the X ray; a plurality of photoelectric conversion elements corresponding to each pixel and configured to detect a plurality of photons included in the light converted by the scintillator and output a first signal; a discriminator configured to discriminate the first signal by at least one threshold value for discriminating whether or not an energy value of the photons indicated by the first signal falls within a range of a predetermined energy value and output a second signal corresponding to the first signal when the energy value of the photons indicated by the first signal falls within the range of the predetermined energy value; and a photon number counting portion configured to count the number of the photons corresponding to the range of the predetermined energy value based on the second signal output based on the first signal discriminated by the threshold in the discriminator.

With this, in each pixel of the grating detection portion, when the energy value of the photon to be detected falls within the range of the predetermined energy value, the number of photons can be counted. As a result, for example, it is possible to count only the number of photons corresponding to a high (low) energy X-ray and acquire an X-ray image of high (low) energy. Therefore, by appropriately setting the threshold values, it is possible to acquire an X-ray image having a desired energy value.

In the X-ray inspection apparatus according to the second aspect of the present invention, it is preferably configured such that the grating detection portion provided at the third grating which absorbs the X-ray and shields the X-ray at the position where the grating image is generated is configured to also serve as the transmitted X-ray detection portion.

With this, unlike the case in which the transmitted X-ray detection portion is provided separately from the grating detection portion, the configuration of the X-ray inspection apparatus can be simplified.

In the X-ray inspection apparatus according to the second aspect of the present invention, it is preferably configured such that the grating detection portion provided at the third grating which absorbs and shields the X-ray at the position where the grating image is generated is configured to acquire the phase image of the X-ray transmitted through the subject without relatively moving the third grating with respect to the second grating.

With this configuration, the phase image of the X-ray can be acquired without moving the third grating with respect to the second grating, compared with a fringe scanning method, etc., which acquires a phase image of an X-ray based on a plurality of X-ray images acquired by image-capturing while relatively moving the third grating with respect to the second grating by one cycle of the phase of the X-ray, it is possible to shorten the time required to acquire the phase image of the X-ray.

In the X-ray inspection apparatus according to the second aspect of the present invention, it is preferably configured such that the first grating, the second grating, and the third grating are configured to be movable relative to each other and it is configured so that the X-ray image capturing method can be switched by moving at least one of the first grating, the second grating, and the third grating so as to deviate from the path of the X-ray depending on the grating detection portion provided in at least one of the first grating, the second grating, and the third grating left on the path.

With this, it is possible to switch one X-ray inspection apparatus to image-capturing method of a plurality of types. Specifically, for example, in cases where only the third grating provided with a grating detection portion is left and the first grating and the second grating are moved so as to deviate from the path, the image capturing method can be made to a normal X-ray image capturing (image capturing by a so-called absorption image capturing apparatus) by the grating detection portion of the third grating.

In the X-ray inspection apparatus according to the second aspect of the present invention, it is preferably configured such that the X-ray inspection apparatus is configured to include a computer tomography apparatus for capturing an X-ray image of the subject by rotating the X-ray irradiation portion, the first grating, the second grating, the third grating, and the transmitted X-ray detection portion at the time of image-capturing around the subject.

With this configuration, it is possible to configure a computer tomography apparatus capable of suppressing the excessive exposure of the subject and the increase in image-capturing time due to the absorption of the irradiated X ray by the grating.

In the radiation grating detector in which the detector includes a plurality of detection elements according to the first aspect of the present invention, it is preferably configured to further include a readout circuit for reading out a plurality of electric signals based on radiation respectively output from each of a plurality of pixels included in the detection portion.

With this, an electric signal based on the incident X-ray is read out by the readout circuit provided in the radiation grating detector. Thus, processing can be performed based on the read information (signal). That is, there is no need to separately provide a readout circuit in the grating detection portion, so that the apparatus configuration of the X-ray inspection apparatus can be simplified.

In the radiation grating detector in which the detection portion includes a plurality of detection elements according to the first aspect of the present invention, it is preferably configured such the plurality of detection elements is arranged in a plurality of lines so that the pitch between them is 1 µm or more and 500 µm or less and the width in a direction intersecting with the line-like arrangement direction of the plurality of grating portions is configured to be ¼ or more and ¾ or less of the pitch.

With this configuration, the detection elements are arranged so that the pitch between them is 1 µm or more and 500 µm or less, which are relatively small. Therefore, the size of the pixel corresponding to the pitch of the detection element can be made sufficiently small to obtain a fine X-ray image. Further, since the width in a direction intersecting with the line-like arrangement direction of the plurality of grating portions is configured to be ¼ or more and ¾ or less of the pitch. Therefore, the size of the width of the opening portion (portions other than the grating portions) that transmits radiation and the size of the width of the line-shaped grating portion which is a non-opening portion that absorbs the radiation (or modulates the phase of radiation) fall within three times in maximum. Therefore, the difference between the width of the opening portion and the width of the grating portion does not become extremely large, and therefore it is possible to make them properly function as gratings for radiation.

In the radiation grating detector according to the first aspect of the present invention, it is preferably configured such that in at least one of the first grating, the second grating, and the third grating, it is provided on the side opposite to the side on which radiation of each detection portion is incident, and it further includes an absorption member for absorbing radiation or modulating the phase of radiation.

With this, even in cases where it is difficult to adequately absorb the radiation or modulate the phase of the radiation on the side of each grating detection portion on which the radiation is incident, it is possible to absorb the X-ray or modulate the phase of the X-ray by the absorption member provided on the side opposite to the side of the grating detection portion on which the X ray is incident.

BRIEF DESCRIPTION OF THE DRAWINGS

FIGS. 8A to 8H each are a diagram for explaining grating detection portions according to modified embodiments of the first to third embodiments of the present invention.

DESCRIPTION OF PREFERRED EMBODIMENTS

Hereinafter, embodiments of the present invention will be described with reference to the attached drawings.

First Embodiment

Initially, a configuration of an X-ray inspection apparatus 100 according to a first embodiment of the present invention will be described with reference to FIG. 1, FIG. 2A, and FIG. 2B.

Overall Configuration of First Embodiment

Figure 1:
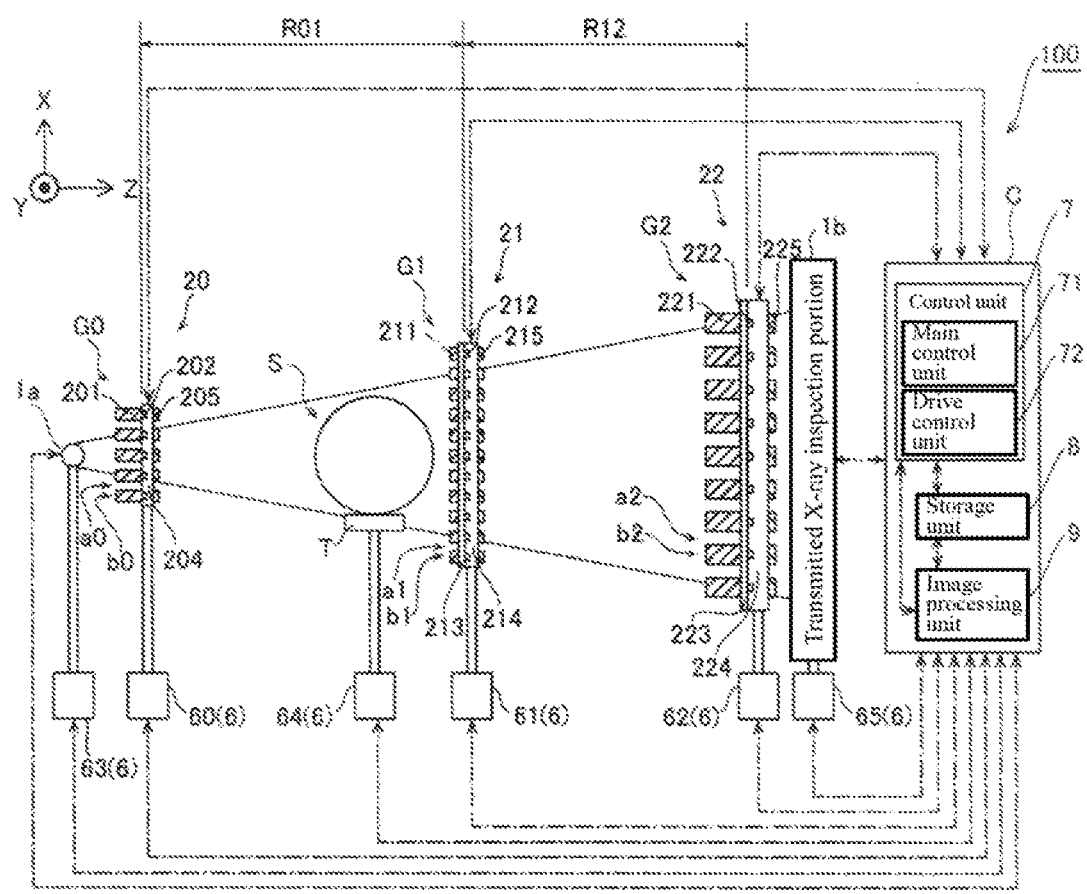
FIG. 1 is a diagram showing a configuration of an X-ray inspection apparatus according to a first embodiment of the present invention.

As shown in FIG. 1, the X-ray inspection apparatus 100 according to the first embodiment includes an X-ray irradiation portion 1*a*, a grating G0, a grating G1, a grating G2, a transmitted X-ray detection portion 1*b*, a moving mechanism 6, a control unit 7, a storage unit 8, an image processing unit 9, and a platform T. Further, as shown in FIGS. 2A and 2B, the grating G0, the grating G1, and the grating G2 are provided with readout circuits 30, 31, and 32, respectively. Note that the grating G0, the grating G1, and the grating G2 are examples of the "first grating", the "second grating" and the "third grating" recited in claims, respectively, and an example of the "radiation grating detector" recited in claims.

As shown in FIG. 1, a subject S is placed on the platform T.

The X-ray irradiation portion 1*a* includes an X-ray tube, etc., and is configured to irradiate an X-ray to the subject S. Further, the X-ray irradiated from the X-ray irradiation portion 1*a* reaches (passes through) the grating G0, the subject S, the grating G1, the grating G2, and the transmitted X-ray detection portion 1*b* in the order thereof. Note that an X-ray is an example of the "radiation" recited in claims. Also note that an X-ray image is an example of the "radiation image" recited in claims.

The grating G0 is configured so as to provide an effect such as an effect of making an incident X-ray irradiated from the X-ray irradiation portion 1*a* into multiple light sources (making a state in which light sources each having a small focal spot size are arranged). In the first embodiment, the grating G0 includes an opening portion a0 through which an X ray passes and a grating portion b0 constituting a non-opening portion other than the opening portion a0, which constitute the grating G0, and a grating detection portion 20 for detecting an incident X-ray transmitted through the grating portion (non-opening portion) b0.

Further, the grating G1 is configured so as to generate a grating image of an incident X-ray transmitted through the subject S. Further, in the first embodiment, the grating G1 includes an opening portion a1 constituting the grating G1 through which an X ray passes, a grating portion b1 constituting a non-opening portion other than the opening portion a1, and a grating detection portion 21 for detecting an incident X-ray transmitted through the grating portion b1.

Further, the grating G2 is configured so as to generate a grating image of the incident X-ray transmitted through the subject S. Further, in the first embodiment, the grating G2 includes an opening portion a2 through which an X ray passes and a grating portion b2 constituting a non-opening portion other than the opening portion a2, which constitute the grating G2, and a grating detection portion 22 for detecting the incident X-ray transmitted through the grating portion b2.

The grating detection portions 20, 21 and 22 are provided on element substrate 204, 214 and 224, respectively. In addition, the element substrates 204, 214, and 224 are each made of, for example, silicon. Further, the surfaces (element substrates 204, 214, and 224) of the grating G0, the grating G1, and the grating G2 are arranged perpendicular to the irradiation direction of the X-ray and horizontally (in the X-Y plane). The grating portions b0, b1, and b2, which are the non-opening portions of the grating G0, the grating G1, and the grating G2, are arranged so that the extending directions of the grating portions b0, b1, and b2 are parallel to each other (Y direction). Note that the grating detection portions 20, 21, and 22 each are an example of the "detection portion" recited in claims.

In the first embodiment, the grating detection portions 20, 21, and 22 each include a scintillator 201, 211, and 221 that converts an incident X-ray into light having a frequency lower than a frequency of the X-ray. The grating detection portions 20, 21, and 22 respectively include photoelectric conversion elements 202, 212, and 222 which are detection elements corresponding to respective pixels and are configured to indirectly detect an X-ray incident on the non-opening portions (grating portion b0, b1, and b2) and output an electric signal. Specifically, the photoelectric conversion elements 202, 212, and 222 each convert the X-ray incident on the non-opening portion (grating portion b0, b1, and b2) by each of the scintillators 201, 211, and 221 into low frequency light (photon) and output an electric signal.

It is configured such that the size of each pixel of the grating detection portions 20, 21, and 22 is smaller than the size of each pixel of the transmitted X-ray detection portion 1b (which will be described later). That is, a high resolution X-ray image is captured (acquired) by the grating detection portions 20, 21, and 22, and a low resolution X-ray image is captured (acquired) by the transmitted X-ray detection portion 1b. The scintillator is made of, for example, CsI (cesium iodide), NaI (sodium iodide), GSO ($Gd_2SiO_5$), GOS ($Gd_2O_2S$), GPS ($Gd_2Si_2O_7$), and the like.

In the first embodiment, in the grating portions b0 and b2 constituting the respective grating G0 and grating G2, the thicknesses of the scintillator 201 and 221 in the incident direction (Z direction) of the X ray is increased so as to function as an absorption grating that absorbs an incident X-ray to prevent transmission of the incident X-ray. Specifically, the thickness (Z direction) of the scintillator 201 and 221 is formed to be about 200 μm or more. With this, the grating G0 and the grating G2 each function as an absorption grating which hardly transmits an X-ray incident on the grating portion (non-opening portion) b0 and b2.

In the first embodiment, in the grating portion b1 constituting the grating G1, the thickness of the scintillator 211 in the X-ray incident direction (Z direction) is reduced so as to function as a phase grating that changes the phase of the incident radiation. Specifically, the scintillator 211 is formed so that the thickness (Z direction) thereof becomes about 1 μm to about 10 μm. As a result, the grating G1 functions as a phase grating that modulates (for example, shifts the phase relatively by π or π/2 with respect to the X-ray transmitted through the opening portion a1) the phase of the X-ray that transmitted through the grating portion (non-opening portion) b1.

Further, in the first embodiment, the grating G1 and the grating G2 are provided with transparent substrates 213 and 223 that allow transmission of an X-ray to which scintillators 211 and 221 are provided, respectively. The transparent substrate 213 (223) is detachably attached to the element substrate 214 (224) provided with the photoelectric conversion element 212 (222) together with the scintillator 211 (221). The transparent substrates 213 and 223 are each made of, for example, glass. Further, the transparent substrate 213 (223) and the element substrate 214 (224) are bonded (tightly adhered) with optical adhesive (grease that transmits light, etc.). In order to suppress diffusion of light converted from an X-ray in the scintillator 211 (221), the scintillator 211 (221) and the photoelectric conversion element 212 (222) are arranged so that the distance thereof is 100 μm or less.

Further, in the first embodiment, each of the grating G0, the grating G1, and the grating G2 is provided with absorption members 205, 215, and 225 for absorbing X-rays on the side (transmitted X-ray detection portion 1b side) opposite to the side (X-ray irradiation portion 1a side) where an X-ray is incident in each grating detection portions 20, 21, and 22. Note that the absorption members 205, 215, and 225 are each preferably made of metal having a large atomic weight in which the absorption of the X-ray is large particularly when used for an absorption grating, for example, gold (Au), platinum (Pt), rhodium (Rh), ruthenium (Ru), iridium (Ir), indium (In), or the like. The material, thickness, etc., of the absorption member 205, 215, and 225 is adjusted so as to obtain desired X-ray absorption or desired X-ray phase modulation as an absorption grating or a phase grating.

Figures 2A, 2B:
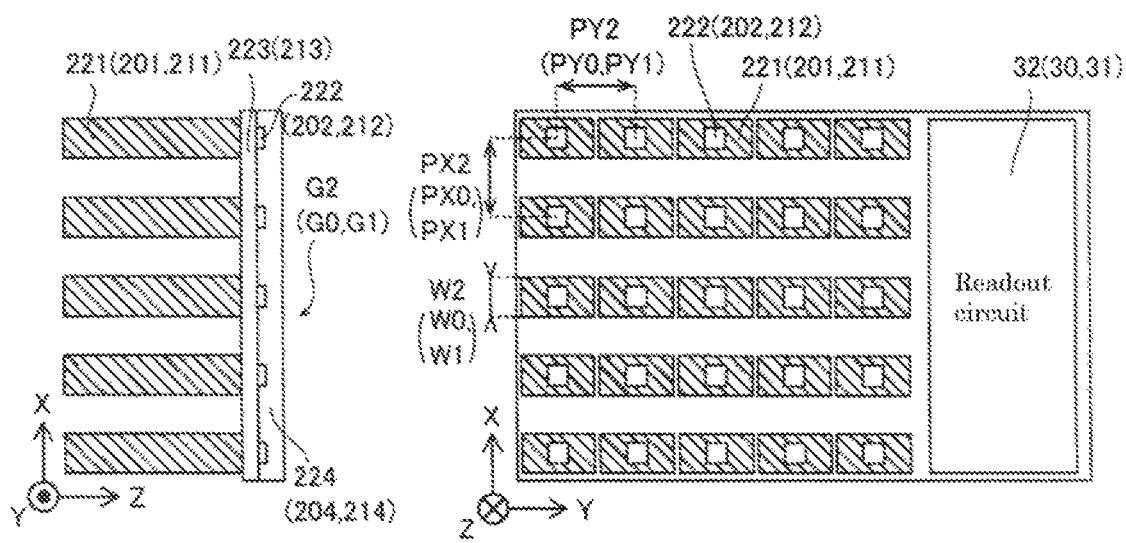
FIGS. 2A and 2B each are a diagram for explaining a grating detection portion and a readout circuit according to the first embodiment of the present invention.

Further, as shown in FIGS. 2A and 2B, in the first embodiment, readout circuits 30, 31, and 32 each for reading out a plurality of electric signals due to X-rays to be output from each of the plurality of pixels included in each of the grating detection portions 20, 21, and 22 are provided. As a result, each of the readout circuits 30, 31, and 32 receives a first signal output from each of the photoelectric conversion elements 202, 212, and 222 in a manner as to distinguish the position (each position of the photoelectric conversion elements 202, 212, and 222) where the photon is detected. The readout circuits 30, 31, and 32 are integrated with the grating G0, the grating G1, and the grating G2, respectively, by being provided, for example, to the element substrates 204, 214, and 224.

In the first embodiment, the plurality of photoelectric conversion elements 202, 212, and 222 are arranged in multiple lines so that the pitch between them is 1 μm or more and 500 μm or less. Further, the width W0, W1, and W2 of the grating portion b0, b1, and b2 in a direction (X direction) orthogonal to the direction (Y direction) of the linear arrangement thereof is configured to be ½ of the pitch. Specifically, the pitch PY0, PY1, and PY2 in the line direction (Y direction) of the photoelectric conversion element 202, 212, and 222 is configured to be 1 μm or more and 500 μm or less. Further, the pitch PX0, PX1, and PX2 in the direction (X direction) orthogonal to the line direction of the photoelectric conversion element 202, 212, and 222 is configured to coincide with the pitch PY0, PY1, and PY2. That is, the photoelectric conversion elements 202, 212, and 222 are arranged to be arranged at equal intervals in the X direction and the Y direction.

Further, the X direction width of the scintillator 201, 211, and 221 constituting the grating portion b0, b1 and b2 is configured to be half (½) of the width of the pitch PX0, PX1 and PX2. Note that the X-ray inspection apparatus 100 can be configured to function as a noninterference type apparatus (non-Talbot Lau interferometer) in which the transmitted X-ray does not cause interference when the pitch PX in the direction orthogonal to the line direction is increased or the absorption is increased by increasing the thickness of the scintillator 211 especially in the grating G1.

The Y direction width of the scintillator 201, 211, and 221 is set such that the scintillators 201, 211, and 221 are arranged with a slight gap in the Y direction. With this, the light (photon) converted by one of the scintillators 201, 211, and 221 is incident on another adjacent scintillator 201, 211, and 221 and detected, which can suppress the detection position of the light (photon) from becoming uncertain. Note that a reflective member that reflects light may be provided in the gap portion in the Y direction.

As shown in FIG. 1, the transmitted X-ray detection portion 1b is configured to detect an X-ray irradiated from the X-ray irradiation portion 1a and transmitted through the grating G0, the subject S, the grating G1, and the grating G2 in this order.

The moving mechanism 6 includes moving mechanisms 60, 61, 62, 63, 64, and 65 capable of making the position of the grating G0, the grating G1, the grating G2, the X-ray irradiation portion 1a, the platform T, and the transmitted X-ray detection portion 1b move in parallel to the X, Y, and Z direction, tilt (rotate) about the X-axis and the Y-axis, rotate about the Z-axis. Note that the position of the stage can be controlled with high accuracy of, e.g., 0.1 μm or 0.01 degrees.

The control unit 7, the storage unit 8, and the image processing unit 9 are provided in the housing C. The control unit 7, the storage unit 8, and the image processing unit 9 are configured so that information (signals) can be exchanged with each other, and are also configured so as to be able to exchange information (singles) with the X-ray irradiation portion 1a, the transmitted X-ray detection portion 1b, the readout circuits 30, 31, and 32, and the moving mechanisms 60 to 65. Note that the dot-and-dash line in the figure indicates that signal (information) exchange is being performed.

The control unit 7 is constituted by an information processing apparatus, such as, e.g., a personal computer (PC). Further, the control unit 7 includes a main control unit 71, such as, e.g., a CPU (central processing unit), and a drive control unit 72. The main control unit 71 causes the PC to function as the control unit 7 of the X-ray inspection apparatus 100 by executing the control program stored in the storage unit 8 (which will be described later). The drive control unit 72 controls the irradiation intensity of the X-ray irradiation portion 1a and the position by the moving mechanism 6 (60 to 65).

The storage unit 8 is composed of an HDD (hard disk drive), a memory, etc., and configured to store the captured X-ray image, the X-ray image processed by the image processing unit 9 (which will be described later), etc. In the storage unit 8, various programs to be executed by the main control unit 71 and the drive control unit 72 are stored.

The image processing unit 9 acquires an X-ray image based on the information (detected signal) of the X-ray (X-ray converted photon) to be acquired by each detection portion (the grating detection portion 20, 21, and 22, and the transmitted X-ray detection portion 1b). Further, the image processing unit 9 acquires the X-ray absorption image from the X-ray information and also acquires the X-ray phase image and the X-ray dark field image by subjecting the pixel value of each pixel to calculation processing, etc.

As described above, the grating G1 functions as a phase grating, and the grating G0 and the grating G2 each function as an absorption grating. That is, the X-ray inspection apparatus 100 constitutes a Talbot-Lau interferometer. Also, the distance R01 between the grating G0 and the grating G1, the distance R12 between the grating G1 and the grating G2, the pitch PY0, PY1, and PY2 in the Y direction of the grating portion b0, b1, and b2 of the grating G0, the grating G1, and the grating G2, and the value of the magnitude, etc., of the phase modulation in the grating G1 must be properly set so that the X-ray inspection apparatus 100 functions as a Talbot-Lau interferometer. The relational expressions and the like that hold between the values will be omitted.

(Acquisition of X-Ray Image and Processing of X-Ray Image)

Hereinafter, acquisition of an X-ray image and processing of an X-ray image by the X-ray inspection apparatus 100 will be described.

First, acquisition of an X-ray image by normal Talbot interference will be explained. In the initial state (at the start of image-capturing), it is assumed that the X-ray transmitted bright portion among bright and dark fringes reflecting the grating portion b1 of the grating G1 (self-image which is a grating image) of the Talbot image generated by the grating G1 completely overlaps with the grating portion b2 of the grating G2. At this time, although the X-ray is shielded by the grating G2, the X-ray scattered or phase-modulated by the subject S is transmitted by deviating from the shielding portion. With this, in the transmitted X-ray detection portion 1b, a moire fringe image of the X-ray transmitted through the subject S is obtained. Note that the Talbot image is one example of the "grating image" recited in claims.

Here, when the grating G2 is slightly moved with respect to the grating G1 in a direction (X direction) perpendicular to the extending direction (Y direction) of the grating portion b2 of the grating G2, in the transmitted X-ray detection portion 1b, a moire fringe image (absorption image) of the X ray in which the bright portion of the Talbot image (self-image) and the grating portion b2 of the grating G2 are shifted (the X-ray is transmitted through the shifted portion grating portion) can be obtained. Similarly, while moving the grating G2 in the vertical direction (X direction) until the bright portion of the Talbot image (self-image) overlaps the grating portion b2 of the grating G2 again (up to one period of the X-ray phase), a plurality of moire fringe images (step curves of each pixel) is acquired in the transmitted X-ray detection portion 1b.

Then, in the image processing unit 9, in each pixel of a plurality of moire fringe images (absorption images) acquired in this manner, an absorption image is obtained by acquiring a pixel value (luminance value) of the pixel, a phase image is obtained by acquiring the phase change of the pixel value (luminance value) of the pixel, and a dark field image is obtained by acquiring a change in the contrast (sharpness) of the pixel value (luminance value) of the pixel. A method of acquiring such an X-ray image is called a fringe scanning method. The absorption image, the phase image, and the dark field image can respectively image-capture different structures of the subject S. The absorption image, the phase image, and the dark field image may be obtained by using a Fourier transform method which acquires a moire fringe image by rotating the face of the grating G2 with respect to the grating G1.

In the first embodiment, in addition to the above X-ray image, it is possible to further acquire an X-ray image to be captured in the grating detection portion 20, 21, and 22 provided in the grating portion (non-opening portion) b0, b1, and b2 of the grating G0, the grating G1, and the grating G2.

Here, in the first embodiment, the grating detection portion 21 provided in the grating G1 is configured to detect the X-ray transmitted through the subject S placed in front of the grating G1. Also, the subject S is placed close to the grating G1 to suppress as much as possible occurrence of edge blurring (blurring by a semi-shadow of the end portion (contour line) of the imaged subject S due to the fact that the X-ray source (light source) has a size).

Specifically, the X-ray image obtained by the grating detection portion 21 (grating G1) is relatively close in distance from the X-ray irradiation portion 1a and low in magnification ratio, so that the distance from the subject S is relatively close and the edge blurring is less. Further, the X-ray image obtained by the grating detection portion 21 is high in resolution (high in definition) since the pixel size of the grating detection portion 21 is relatively small. The X-ray image obtained by the grating detection portion 21 is an absorption image of the subject S.

In the first embodiment, it may be configured such that the temporal fluctuation of the intensity of the X-ray irradiated by the X-ray irradiation portion 1a, which is detected by the grating detection portions 20, 21, and 22 provided to the grating G0, the grating G1, and the grating G2, is acquired and the luminance of the X-ray image acquired at different times is corrected on the basis of the obtained temporal fluctuation of the intensity so that the luminance becomes constant.

In particular, in cases where the luminance of the X-ray image captured (acquired) by the grating detection portion 20, 21, and 22 (the average luminance of the entire pixel or the luminance (maximum luminance) of the pixel where a direct line which does not pass through the subject S is incident) becomes larger (smaller), since the intensity of the X-ray irradiated from the X-ray irradiation portion 1a is increased (decreased), by reducing (increasing) the overall luminance of the X-ray image by the image processing unit 9, the image processing unit 9 corrects so that the brightness (luminance) between the X-ray images captured at different times becomes constant.

Further, in the first embodiment, it may be configured such that, based on the fluctuation of the intensity of the X-ray transmitted through the subject S and detected by the grating detection portions 21 and 22 provided in each of the grating G1 and the grating G2, positional fluctuations of the grating G0, the grating G1, and grating G2 are acquired and the grating G0, the grating G1, and the grating G2 are relatively moved so that the positional fluctuations are corrected.

Specifically, the control unit 7 (drive control unit 72) relatively moves the grating G0, the grating G1, and the grating G2 so that the intensity of the X-ray coincides with the intensity before the positional movements occur. For example, by the positional movement of the contour part of the subject S in the X-ray image captured in the grating G1 (grating detection portion 21) and the positional movement of the bright and dark fringes of the Talbot image (self-image) in the X-ray image captured by the grating G2 (grating detection portion 22), the positional movements, etc., are acquired.

Further, the above-described positional fluctuations occur due to thermal deformation of the flame, the stage, etc., supporting the grating G0, the grating G1, and the grating G2 in accordance with the fluctuation of the heat generated from a stepping motor, etc., included in the X-ray irradiation portion 1a and the moving mechanism 6 and the outside air temperature.

Also, in the first embodiment, it is configured to acquire an X-ray image supplemented in resolution based on the combination of at least two or more images different in resolution among the first X-ray image captured by the grating detection portion 21 provided in the grating G1, the second X-ray image captured by the grating detection portion 22 provided in the grating G2, and the third X-ray image captured by the transmitted X-ray detection portion 1b.

Here, since the high resolution X-ray image becomes relatively small in the size of the pixel, an X-ray image relatively fine in the contour line, etc., of the subject S can be acquired, but the number of photons of the X-ray incident on each pixel decreases. Therefore, the intensity irregularity (noise) of the X-ray irradiated from the X-ray irradiation portion 1a easily occurs. On the other hand, although the X-ray image of low resolution tends to become an X-ray image in which the contour line, etc., of the subject S is blurred, the number of photons of the X-ray incident on each pixel increases. Therefore, even in the case of a short-time image-capturing, the influence of the strength intensity (noise) of an X-ray irradiated from the X-ray irradiation portion 1a is relatively small. By combining a plurality of X-ray images different in resolution which are almost simultaneously obtained for the same subject S, it is possible to acquire an X-ray image with supplemented resolution (noise is reduced and high resolution).

Specifically, for example, the absorption image (first X-ray image) obtained by the grating detection portion 21 is captured at the position closest to the X-ray irradiation portion 1a and the subject S, and therefore it is low in edge blurring, etc., and high in resolution. Further, the phase image (second X-ray image) obtained in the grating detection portion 22 is relatively close to the subject S and high in resolution. By combining these images with the relatively low resolution absorption image and the phase image (third X-ray image) obtained for the same subject S in the transmitted X-ray detection portion 1b, an X-ray image (phase image) high in resolution and reduced in noise, etc., (compared with a single image) can be obtained. Note that three absorption images, etc., may be combined.

In the first embodiment, the grating detection portion 22 provided in the grating G2 is configured to acquire the phase image of the X-ray transmitted through the subject S without moving the grating G2 with respect to the grating G1.

Specifically, the size of each pixel included in the grating G2 is small (about equal to or less than the grating image), and therefore it is possible to detect slight deviation, phase modulation, etc., due to the X-ray scattered by the subject S. For this reason, without forming a moire fringe image, it is possible to image-capture the X-ray phase modulation (X-ray phase image) due to the subject S by directly image-capturing the X ray incident from the grating G1. By moving the grating G2 with respect to the grating G1 (relative movement in the fringe scanning method or the Fourier transform method), in the grating G2 (grating detection portion 22), it is also possible to acquire an absorption image, a phase image, and a dark field image in the same manner as in an ordinary Talbot-Lau interferometer.

Also, in the first embodiment, it is configured so that the X-ray image capturing method can be switched by moving the grating G0, the grating G1, and/or the grating G2 without moving at least one of them so as to deviate from the path of the X-ray, depending on the grating detection portion 20, 21, and 22 provided in the grating G0, the grating G1, and the grating G2 left on the path.

Specifically, for example, by removing (moving) the grating G0 and the grating G1 from the path of the X-ray involved in the image-capturing while maintaining only the grating G2 on the path, it can be made to function as an X-ray inspection apparatus 100 which performs normal X-ray image-capturing (capturing of the absorption image) at the position of the grating G2.

Also, for example, in cases where the X-ray irradiation portion 1a is constituted by a synchrotron radiation device, a micro-focus X-ray source, etc., it is possible to irradiate an X-ray sufficiently high in coherence from the X-ray irradiation portion 1a. Therefore, it is no necessary to reduce the focal spot size by the grating G0, which makes it possible to deviate (move) the grating G0 from the path of the X-ray involved in the image-capturing. When using the grating G0, there is a limitation that the focal spot size of the X-ray irradiated from the X-ray irradiation portion 1a must be made larger than the pitch PY (in the Y direction) of the grating portion b0 of the grating G0. However, by removing the grating G0 from the path of the X-ray and reducing the focal spot size of the irradiated X-ray, it is possible to acquire a high definition image lesser in edge blurring, etc. Note that the X-ray inspection apparatus having such a configuration in which the grating G0 is removed functions as a Talbot interferometer.

In order to configure an X-ray inspection apparatus 100 capable of acquiring a phase image and a dark field image of an X-ray, it is sufficient to arrange at least the grating G1 on the path of the X-ray involved in image-capturing.

Effects of First Embodiment

In the first embodiment, the following effects can be obtained.

In the first embodiment, each of the grating G0, the grating G1, and the grating G2 is configured as described above, and it is configured to provide the opening portions a0, a1, and a2 constituting each of the grating G0, the grating G1, and the grating G2 through which the X-ray transmits, the grating portions b0, b1, and b2 constituting the non-opening portion other than the opening portions, and the grating detection portions 20, 21, and 22 which are provided at the non-opening portions to detect the incident X-ray transmitted through the grating portion b2.

As a result, the radiation absorbed (not transmitted) in the non-opening portion is image-captured by the detection portion, and therefore it becomes possible to utilize the radiation incident on the non-opening portion which was conventionally uselessly irradiated because it was absorbed in each grating portion without reaching the transmitted X-ray detection portion 1b. That is, it possible to provide an X-ray inspection apparatus 100 capable of inspecting the subject S by the X-ray by effectively utilizing the X-ray irradiated to the grating portions (non-opening portions) b0, b1, and b2. For example, in cases where the grating detection portion 20 of the present invention is provided in the grating G0 for aligning the phase of incident radiation, fluctuations in the irradiation intensity of the X-ray can be detected.

Further, in cases where the grating detection portion 21 of the present invention is provided in the grating G1, the X-ray just after transmitted through the subject S can be detected by the grating G1. Therefore, an absorption image with less edge blurring (blurring at the edge of the image-captured subject S) can be acquired.

Further, in cases where the grating detection portion 22 of the present invention is provided in the grating G2 provided at the position where the grating image is generated, the phase image can be directly acquired by the grating G2. It is also possible to effectively utilize the X-ray transmitted through the subject S to image-capture the subject S with the grating G1 and/or the grating G2. Therefore, unlike the case of providing only the transmitted X-ray detection portion 1b that image-captures the X-ray after the absorption (loss) of the X-ray by the grating G1 and the grating G2 has occurred, it is possible to provide an X-ray inspection apparatus 100 capable of reducing the total amount of X-ray to be irradiated to the subject S in order to obtain an X-ray image with necessary sensitivity. As a result, in the X-ray inspection apparatus 100 of the first embodiment, when the subject is a living body, the exposure dose of the subject can be reduced (and the imaging time can be shortened).

In the first embodiment, as described above, in each of the grating detection portions 20, 21, and 22, it is configured to include photoelectric conversion elements 202, 212, and 222 which are a plurality of detection elements corresponding to respective pixels and configured to indirectly detect an X-ray incident on the non-opening portion and output an electric signal (first signal). With this, it is possible to easily capture an X-ray image not only based on the radiation passed through each opening portion a0, a1, and a2 but also based on the X-ray corresponding to each pixel detected by the plurality of photoelectric conversion elements 202, 212, and 222 constituting each of the grating detection portions 20, 21, and 22.

In the first embodiment, as described above, the photoelectric conversion element 202, 212, and 222 which is a detection element is configured to detect low frequency light converted by the scintillator 201, 211, and 221 and output an electric signal (first signal). With this, the X-ray having a high frequency which is strong in transmission force and difficult in directly detection can be converted to low frequency light by the scintillator 201, 211, and 221, and the converted light can be detected by the photoelectric conversion element 202, 212, and 222. For this reason, it becomes possible to easily detect radiation incident on the position of the grating portion (non-opening portion) b0, b1, and b2.

In the first embodiment, as described above, each of the grating portions b0, b1, and b2 functions as an absorption grating that absorbs an incident X-ray so as not to transmit by increasing the thickness of the scintillator 201, 211, and 221 with respect to the incident direction of the X-ray and constitutes the grating G0 and the grating G2, and functions as a phase grating that changes the phase of the incident X-ray by decreasing the thickness of the scintillators 201, 211, and 221 with respect to the X-ray incidence direction and constitutes the grating G1. This allows the scintillators 201, 211, and 221 to easily function as an absorption grating or a phase grating simply by changing the thickness of the scintillators 201, 211, and 221 with respect to the X-ray incident direction.

Further, in the first embodiment, as described above, each of the transparent substrates 203, 213, and 223 is configured so as to be detachably attached to each of the element substrates 204, 214, and 224 provided with the photoelectric conversion elements 202, 212, and 222 together with each of the scintillators 201, 211, and 221. With this, in cases where each of the scintillators 201, 211, and 221 is attached to the element substrates 204, 214 and 224 together with each of the transparent substrates 203, 213 and 223, it can function as a radiation grating detector that performs absorption (or modulation of the X-ray phase) with respect to the X-ray in the grating portions (non-opening portions) b0, b1, and b2 to the incident X-ray and performs image-capturing by the grating detection portions 20, 21 and 22.

Also, in cases where each of the scintillators 201, 211, and 221 is removed from the element substrates 204, 214, and 224 together with each of the transparent substrates 203, 213, and 223, it can function as a normal radiation image capturing apparatus for detecting an X-ray incident on the positions of the grating detection portions 20, 21, and 22.

In the first embodiment, as described above, the readout circuits 30, 31, and 32 for reading out a plurality of electric signals (first signals) based on the X-ray output from each of a plurality of pixels included in each of the grating detection portions 20, 21 and 22. With this, the electric signals (first signals) based on the incident X-ray are read out by the readout circuits 30, 31, and 32 provided in each of the grating detection portions 20, 21, and 22. Thus, processing can be performed based on the read information (first signals). That is, there is no need to separately provide a readout circuit in the grating detection portions 20, 21 and 22, so that the apparatus configuration of the X-ray inspection apparatus 100 can be simplified.

Further, in the first embodiment, as described above, each of the widths W0, W1, and W2 in a direction (X direction) intersecting with the line-like arrangement direction (Y direction) of the plurality of grating portions is configured to be ½ of the pitch PX1, PX2, and PX3. With this, the photoelectric conversion elements 202, 212, and 222 are arranged so that the pitch between them is 1 µm or more and 500 µm or less, which are relatively small. Therefore, the size of the pixel corresponding to the pitch of the photoelectric conversion element 202, 212, and 222 can be made sufficiently small to obtain a fine X-ray image.

Further, since the width in the direction (X direction) intersecting with the line-like arrangement direction (Y direction) of each of the grating portions (non-opening portions) b0, b1, and b2 is configured so that the pitch is ½, the size of the width of the opening portion a0, a1, and a2 (portion other than the grating portion) that transmits an X-ray and the size of the width of the grating portion which is a non-opening portion that absorbs an X-ray (or modulates the phase of radiation) are equal (there is no difference in size). Therefore, the difference between the width of each of the opening portions a0, a1, and a2 and the width of each of the grating portions (non-opening portions) b0, b1, and b2 does not become extremely large, and therefore it is possible to make them properly function as gratings for radiation.

Further, in the first embodiment, as described above, in each of the grating G0, the grating G1, and the grating G2, it is configured to provide an absorption member 205, 215, and 225 for absorbing an X-ray on the side (X-ray irradiation portion 1a side) of the grating detection portion 20, 21, and 22 where an X-ray is incident (transmitted X-detection portion 1b side). With this, even in cases where it is difficult to adequately absorb an X-ray or modulate the phase of an X-ray on the side of the grating detection portion 20, 21 and 22 on which an X-ray of is incident, it is possible to absorb the X-ray or modulate the phase of the X-ray by the absorption member 205, 215 and 225 provided on the side of the grating detection portion 20, 21 and 22 opposite to an X-ray incident side.

In the first embodiment, as described above, the grating detection portion 21 provided in the grating G1 for generating the grating image of the incident X-ray is configured to detect the X-ray transmitted through the subject S disposed in front of the grating G1. With this, since the X-ray transmitted through the subject S is image-captured by the grating detection portion 21 provided in the grating G1 provided relatively close to the X-ray irradiation portion 1a, it is possible to acquire a high definition X-ray image which is relatively few in the edge blurring of the subject S and relatively small in the magnification ratio of the subject S.

Further, since the X-ray is image-captured before the occurrence of the X-ray absorption (loss) by the element substrate 214 of the grating G1 and the grating G2, it is possible to acquire an X-ray image including a soft X-ray (X-ray with relatively low energy). In particular, in cases where the grating G0 does not exist on the path of the X-ray involved in image-capturing, X-ray absorption by the grating G0 does not occur, and therefore an X-ray image including a soft X-ray can be effectively acquired.

Further, in the first embodiment, as described above, it is configured such that the temporal fluctuation of the intensity of the X-ray irradiated by the X-ray irradiation portion 1a, which is detected by the grating detection portions 20, 21, and 22 provided to each of the grating G0, the grating G1, and the grating G2 is acquired and the luminance of the X-ray image acquired at different times is corrected so as to become constant on the basis of the acquired temporal fluctuation of the intensity. With this, even in cases where the intensity of the X-ray irradiated by the X-ray irradiation portion 1a becomes unstable and the luminance of the captured X-ray image fluctuates, it is possible to easily correct the luminance of the X-ray image based on the temporal fluctuation of the intensity of the X-ray irradiated by the acquired X-ray irradiation portion 1a.

In the first embodiment, as described above, it is configured to acquire the positional fluctuation of each of the grating G0, the grating G1, and the grating G2 based on the fluctuation of the intensity of the X-ray transmitted through the subject S detected by the grating detection portions 21 and 22 provided in each of the grating G1 that creates a grating image of the incident X-ray and the grating G2 that shields the X-ray by absorbing the X-ray at the position where the grating image is created, and each of the grating G0, the grating G1 and the grating G2 is relatively moved to correct the positional fluctuation.

With this, even in cases where at least one of the positions of the grating G0, the grating G1, and the grating G2 fluctuates due to any external factor (for example, thermal fluctuation), it is possible to capture a desired X-ray image by correcting the position of each of the grating G0, the grating G1, and the grating G2.

In the first embodiment, as described above, it is configured to acquire an X-ray image in which the resolution is complimented based on a combination of at least two or more X-ray images different in resolution among a first X-ray image captured by the grating detection portion 21 provided in the grating G1 for generating the grating image of the incident X-ray, a second X-ray image captured by the grating detection portion 22 provided in the grating G2 for absorbing and shielding the X-ray at a position where a grating image is generated, and a third X-ray image captured by the transmitted X-ray detection portion 1b. With this, even in cases where the resolution of each of the first X-ray image, the second X-ray image, and the third X-ray image are relatively low, by combining at least two of these X-ray images, it is possible to acquire an X-ray image relatively high in resolution.

In the first embodiment, as described above, the grating detection portion 22 provided in the grating G2 which absorbs and shields the X-ray at the position where the grating image is generated is configured to acquire the phase image of the X-ray transmitted through the subject S without relatively moving the grating G2 with respect to the Grating G1. With this, the phase image of the X-ray can be acquired without moving the grating G2 with respect to the grating G1, compared with a fringe scanning method, etc., which acquires a phase image of an X-ray based on a plurality of X-ray images to be acquired by image-capturing while relatively moving the grating G2 with respect to the grating G1 by one cycle of the phase of the X-ray. Therefore, it is possible to shorten the time required to acquire the phase image of the X-ray.

Further, in the first embodiment, it is configured so that X-ray image capturing methods can be switched by moving the grating G0, the grating G1, and the grating G2 without moving at least one of them so as to deviate from the path of the X-ray, depending on the grating detection portion 20, 21, and 22 provided in at least one of the grating G0, the grating G1, and the grating G 2 left on the path. With this, it is possible to switch one X-ray inspection apparatus 100 to image-capturing methods of a plurality of types. Specifically, for example, in cases where only the grating G2 provided with a grating detection portion is left and the grating G0 and the grating G1 are moved so as to deviate from the path, the image capturing method can be made to a normal X-ray image capturing apparatus (so-called absorption image capturing apparatus) by the grating detection portion 22 of the grating G2.

Second Embodiment

Figure 3:
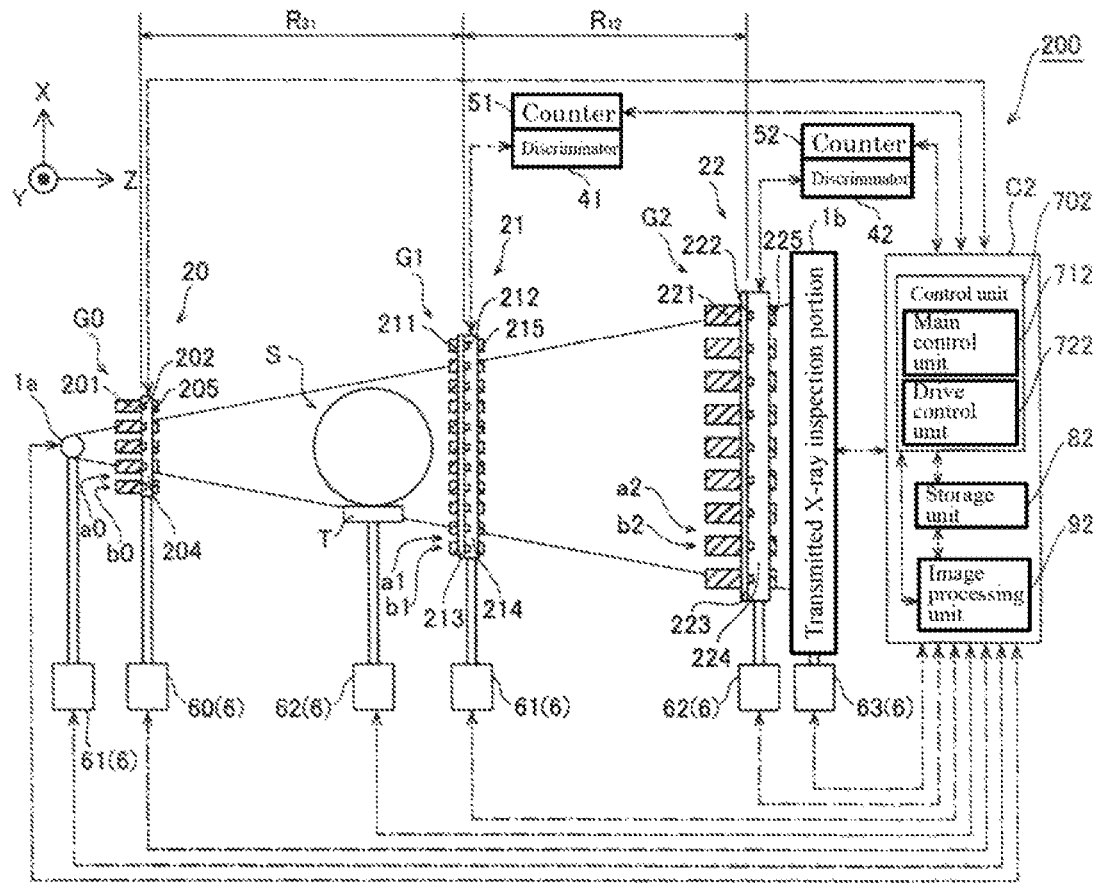
FIG. 3 is a diagram showing a configuration of an X-ray inspection apparatus according to a second embodiment of the present invention.

Next, the configuration of the X-ray inspection apparatus 200 according to a second embodiment will be described with reference to FIG. 3. Unlike the first embodiment, an X-ray inspection apparatus 200 according to the second embodiment is configured to acquire an X-ray image reflecting the composition of the subject S using X-ray images captured by X-rays different in energy.

Here, in the second embodiment, it is configured to acquire an X-ray image reflecting the composition of the subject S based on a combination of at least two or more images captured by X-rays different in energy among the first X-ray image captured by the grating detection portion 21 provided in the grating G1, the second X-ray image captured by the grating detection portion 22 provided in the grating G2, and the third X-ray image captured by the transmitted X-ray detection portion 1b.

Further, in the second embodiment, it is configured as follows. The grating detection portions 21 and 22 are provided in the respective grating G1 and the grating G2. The grating detection portions 21 and 22 are provided with discriminators 41 and 42, respectively. The discriminators 41 and 42 each are configured to discriminate the first signal by threshold values Th1 and Th2 for discriminating whether the value of the energy of photon indicated by the first signal falls within a range of a predetermined energy value every photoelectric conversion element 212 and 222. The discriminators 41 and 42 are further provided with counters 51 and 52 for counting the number of photons corresponding to the range of a predetermined energy value based on the second signal output based on the first signal discriminated by the threshold values Th1 and Th2 in the discriminators 41 and 42. Note that the counter 51 and the counter 52 are examples of the "photon number counting portion" recited in claims.

A control unit 702 including a main control unit 712 and a drive control unit 722, a storage unit 82, and an image processing unit 92 are provided in a housing C2.

Specifically, the X-ray irradiated from the X-ray irradiation portion 1a contains an X-ray having various energy values centered on a representative energy value (the mode value of the histogram). Further, the representative energy value can be increased (decreased) by increasing (decreasing) the voltage of the X-ray tube, etc., included in the X-ray irradiation portion 1a.

Here, the discriminator 41 is connected to the readout circuit 31 (see FIGS. 2A and 2B) of the grating G1. The discriminator 41 discriminates the value of the energy of the X-ray detected by the scintillator 211 provided in the grating G1. That is, when the energy of the detected X-ray is smaller than the threshold value Th1, the discriminator 41 outputs a second signal to the counter 51 based on the first signal output from each of the plurality of photoelectric conversion elements 212 corresponding to each pixel. Further, when the energy of the detected X-rays is larger than the threshold value Th1, the discriminator 41 does not output a second signal to the counter 51. That is, in the grating G1 (grating detection portion 21), a second signal is output to the counter 51 only when an X-ray smaller in energy than a predetermined energy (threshold value Th1) is incident.

Next, the counter 51 counts the number of photons detected at each pixel based on the second signal. As a result, the image processing unit 92 acquires a first X-ray image relatively low in energy based on the X-ray smaller in energy than a predetermined energy (threshold value Th1) based on the number of photons measured.

Further, the discriminator 42 is connected to the readout circuit 32 (see FIGS. 2A and 2B) of the grating G2. The X-ray incident on the grating G2 reaches the grating detection portion 22 (without being lost by absorption) by being transmitted through the element substrate 214, etc., of the grating G1, and therefore is an X-ray (hard X-ray) having a relatively high energy at the time of incident on the subject S. Therefore, the discriminator 42 is configured to output the second signal when an X-ray (grating) smaller in energy value than the threshold Th2 corresponding to the energy value higher than the threshold Th1 is incident. The counter 52 counts the number of incident gratings based on the second signal. Accordingly, similarly, the image processing unit 92 acquires a second X-ray image having moderate energy based on the X-ray including an X-ray larger in energy than the threshold value Th1 and smaller in energy than a predetermined energy (threshold value Th2).

As described above, it is configured such that the detection of the photon counting method can be made by connecting the counters 51 and 52 (via the discriminators 41 and 42) to each of the grating detection portions 21 and 22.

Further, the transmitted X-ray detection portion 1b captures an X-ray having a higher energy value that transmits through the element substrate 224 of the grating G2 and incident, and therefore obtains a third X-ray image of relatively high energy.

Here, the absorption of the X-ray by the subject S (the attenuation of the X ray that transmits through the subject) differs depending on the composition of the portion of the subject S through which the X-ray transmits and the value of the energy (frequency) of the incident X ray. Therefore, for example, in the first X-ray image acquired by the grating detection portion 21, even if the luminance of certain two pixels are the same, the composition of the subject S is not always the same. However, in cases where the composition of the subject S differs in the respective pixels, in the second X-ray image (third X-ray image) acquired based on the X-ray having energy different from the energy in the grating detection portion 21 at the grating detection portion 22 (transmitted X-ray detection portion 1b), when corresponding two pixels are different in luminance, it is considered that the composition of the subject S differs at respective pixel positions.

Further, conventionally, since an X-ray was detected by one detection portion, it was necessary to irradiate (representative energy of) X-rays at least twice with high energy and with low energy. However, in the second embodiment, as described above, a plurality of images (first to third X-ray images) corresponding to different X-ray energies are image-captured with one irradiation at the plurality of detection portions (the grating detection portions 21 and 22 and the transmitted X-ray detection portion 1b). Therefore, the total irradiation dose of an X-ray can be suppressed. Further, by combining the first to third X-ray images, it is possible to display regions (for example, bones in a human body or metal portions in a part, etc.) made of a specific composition of the subject S while emphasizing or excluding them.

Effects of Second Embodiment

In the second embodiment, the following effects can be obtained.

In the second embodiment, as described above, it is configured to acquire an X-ray image in which the composition of the subject S is reflected based on a combination of at least two or more X-ray images captured with X-rays different in energy among a first X-ray image captured by the grating detection portion 21 provided in the grating G1 for generating the grating image of the incident X-ray, a second X-ray image captured by the grating detection portion 22 provided in the grating G2 for absorbing and shielding the X-ray at a position where a grating image is generated, and a third X-ray image captured by the transmitted X-ray detection portion 1b. With this, even in cases where each of the first X-ray image, the second X-ray image, and the third X-ray image does not reflect the composition of the subject S, by combining at least two of these X-ray images, it is possible to acquire an X-ray image reflecting the composition of the subject S.

Further, in the second embodiment, as described above, each of the grating detection portions 21 and 22 provided in the grating G1 for generating a grating image of an incident X-ray and in the grating G2 for absorbing and shielding the X-ray at the position where the grating image is generated is configured to provide with the discriminators 41 and 42 and the counters 51 and 52. The discriminators 41 and 42 discriminate the first signal by at least one of the threshold values Th1 and Th2 for discriminating whether or not the energy value of the photon indicated by the first signal falls within the range of the predetermined energy value for each photoelectric conversion element 212 and 222. The counters 51 and 52 count the number of photons corresponding to the range of a predetermined energy value based on the second signal output based on the first signal discriminated with the threshold value in each of the discriminators 41 and 42.

With this, in each pixel of the grating detection portions 21 and 22, when the energy value of the photon detected falls within the range of the predetermined energy value, the number of photons can be counted. As a result, for example, it is possible to count only the number of photons corresponding to a high (low) energy X-ray and acquire an X-ray image of high (low) energy. Therefore, by appropriately setting the threshold values Th1, Th2, etc., it is possible to acquire an X-ray image having a desired energy value.

Other configurations and effects of the second embodiment are the same as those of the first embodiment.

Third Embodiment

Figure 4:
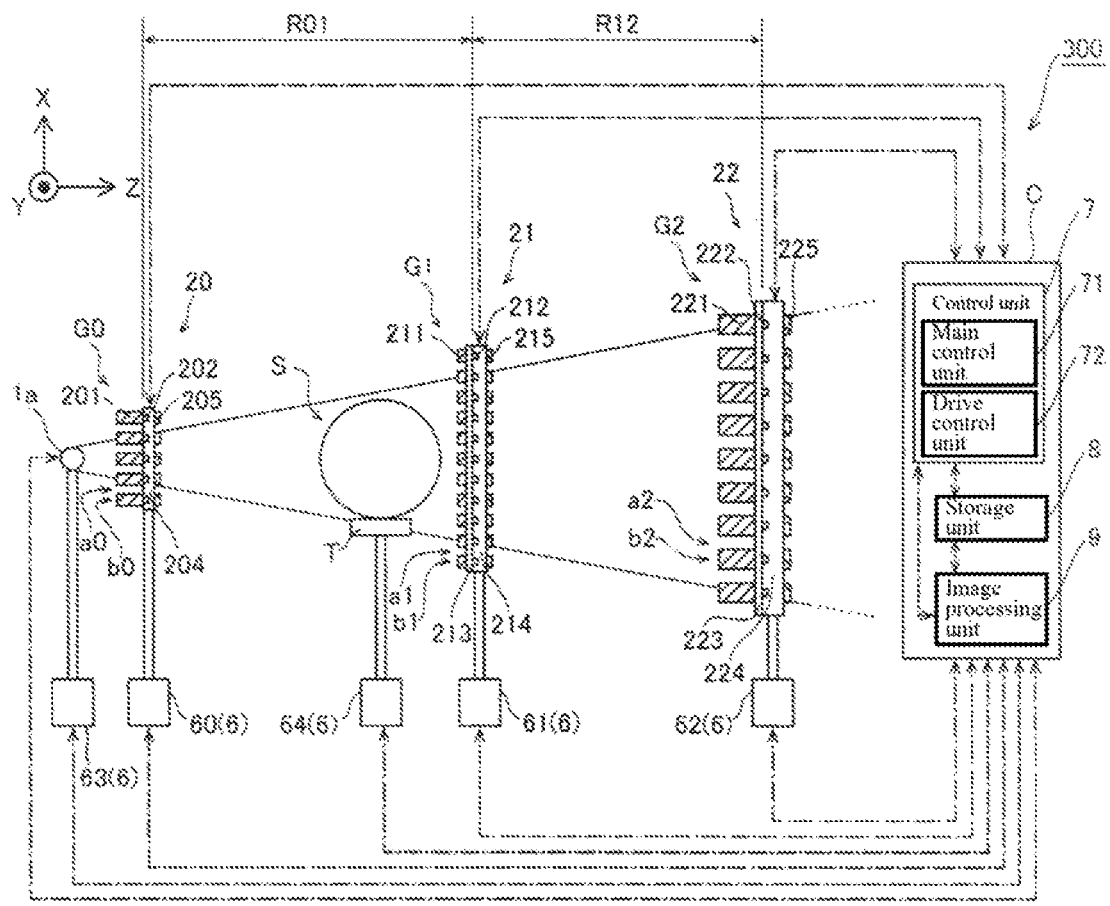
FIG. 4 is a diagram showing a configuration of an X-ray inspection apparatus according to a third embodiment of the present invention.

Next, the configuration of the X-ray inspection apparatus 300 according to a third embodiment will be described with reference to FIG. 4. Unlike the first embodiment, the X-ray inspection apparatus 300 according to the third embodiment is not provided with the transmitted X-ray detection portion 1b.

Here, in the third embodiment, the grating detection portion 22 provided in the grating G2 is configured to also serve as the transmitted X-ray detection portion 1b.

Specifically, since an absorption image, a phase image, and a dark field image can be directly acquired by the grating G2, it is possible to adopt a configuration in which the transmitted X-ray detection portion 1b is omitted.

Effects of Third Embodiment

In the third embodiment, as described above, the grating detection portion 22 provided in the grating G2 which absorbs and shields the X-ray at the position where the grating image is generated is configured to also serve as the transmitted X-ray detection portion 1b (in the first embodiment). With this, unlike the case in which the transmitted X-ray detection portion 1b is provided separately from the grating detection portion 22, the configuration of the X-ray inspection apparatus 100 can be simplified.

Other configurations and effects of the third embodiment are the same as those of the first embodiment.

Fourth Embodiment

Figure 5:
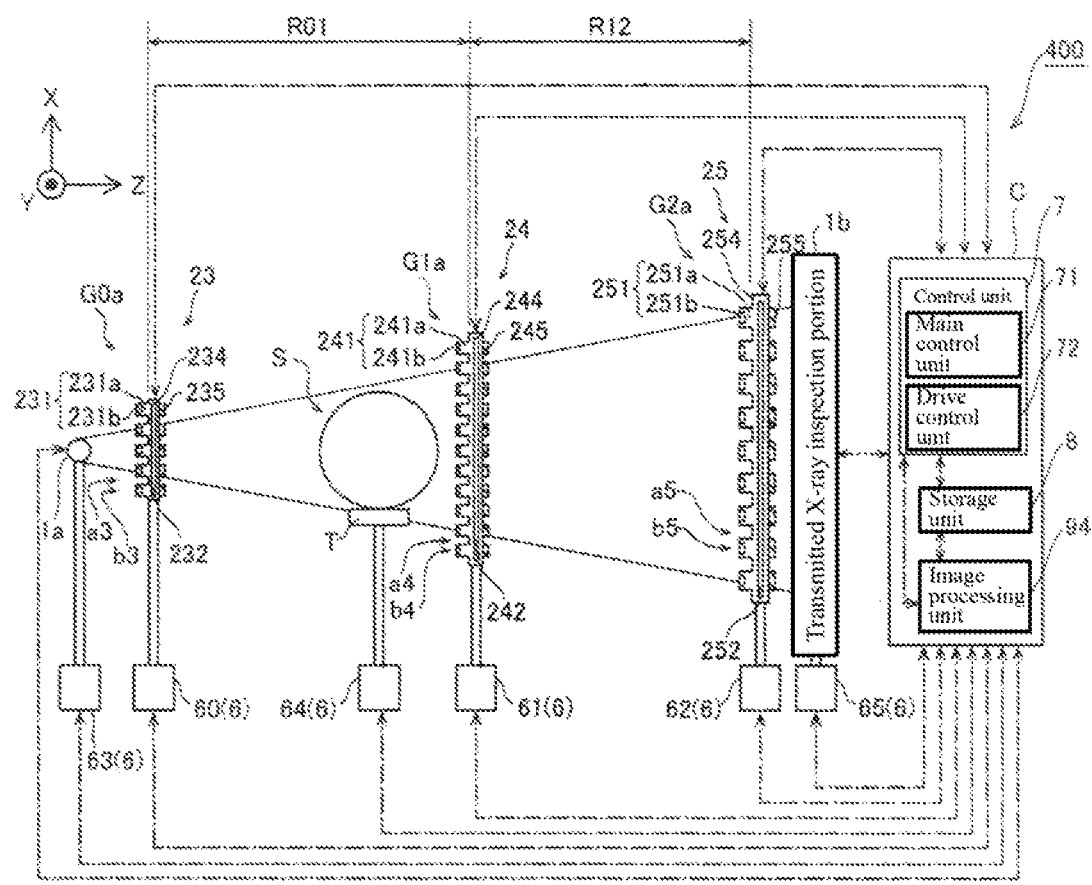
FIG. 5 is a diagram showing a configuration of an X-ray inspection apparatus according to a fourth embodiment of the present invention.
Figure 6A:
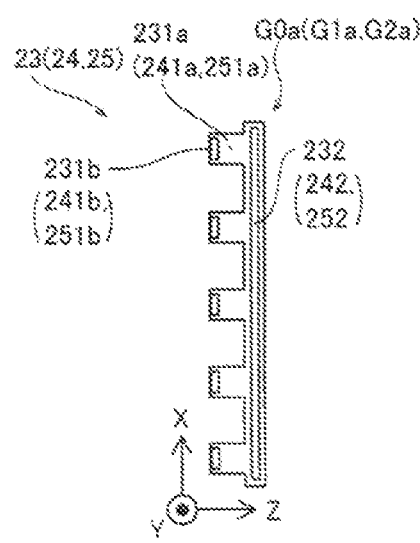
FIGS. 6A and 6B each are a diagram for explaining a grating detection portion and a readout circuit according to the fourth embodiment of the present invention.
Figure 6B:
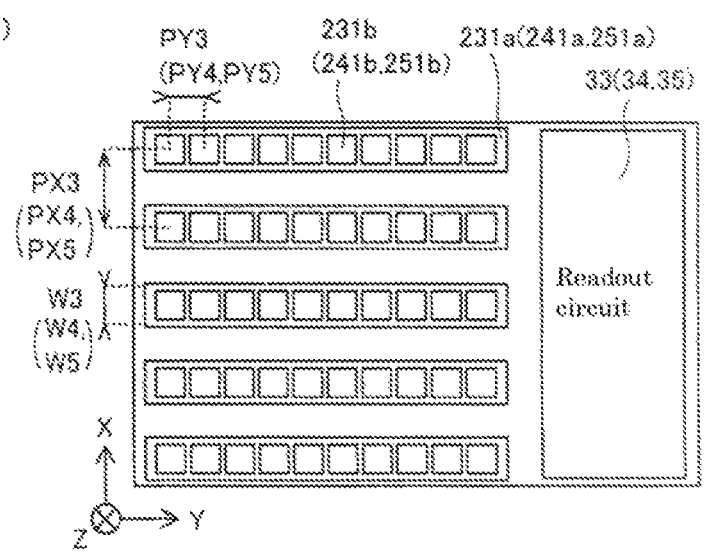

Next, the configuration of the X-ray inspection apparatus 400 according to a fourth embodiment will be described with reference to FIG. 5, FIG. 6A, and FIG. 6B. In the X-ray inspection apparatus 400 according to the fourth embodiment, unlike the first embodiment, semiconductor detection elements 231, 241, and 251 are provided at a grating detection portion 23 of a grating G0a, each grating detection portion 24 of the grating G1a, and a grating detection portion 25 of a grating G2a, respectively. Note that the grating G0a, the grating G1a, and the grating G2a are examples of the "first grating", the "second grating", and the "third grating" recited in claims.

Here, in the fourth embodiment, the semiconductor detection elements 231, 241, and 251, which are detection elements, each include a semiconductor conversion film 231a, 241a, and 251a that convert an incident X-ray into currents and electrodes 231b, 241b, and 251b that output the current signal converted by the semiconductor conversion film 231a, 241a, and 251a. Further, the element substrates 234, 244 and 254 provided with the respective semiconductor detection elements 231, 241, and 251 are provided with electrodes 232, 242, and 252 paired with the electrodes 231b, 241b, and 251b.

Specifically, the X-rays incident on the respective grating portions b3, b4, and b5 react with the respective semiconductor conversion films 231a, 241a, and 251a to generate electrons or holes. Each generated electron or hole turns into a current (first signal) by a voltage applied between the electrode 231b (241b, 251b) and the electrode 232 (242, 252). That is, the incident X-ray is directly converted into an electric signal.

Further, in the fourth embodiment, each of the grating portions (non-opening portions) b3 and b5 constituting the grating G0a and the grating G2a is configured so as to function as an absorption grating that absorbs the incident X-ray so as not to transmit therethrough by making the electrodes 231b and 251b thicker and composing the materials of the semiconductor conversion films 231a and 251a by heavy elements. Further, the grating portion (non-opening portion) b4 constituting the grating G1a is configured to function as a phase grating that changes the phase of the incident X-ray by thinning the electrode 241b and composing the material of the semiconductor conversion film 241a by a light element. It should be noted that opening portions a3, a4, and a5 of the grating G0a, the grating G1a, and the grating G2a are configured to transmit incident X-rays almost without causing absorption or phase modulation.

Specifically, in order to make the grating G0a and the grating G2a function as an absorption grating, the semiconductor conversion films 231a and 251a are made of, for example, relatively heavy Se (selenium), CdTe (cadmium telluride), or CZT (CdZnTe: cadmium telluride Zinc). Further, the electrodes 231b and 251b are formed to be relatively thick. Further, in order to make the grating G1a function as a phase grating, the semiconductor conversion film 241a is made of, for example, Si (silicon). Further, the electrode 241b is formed to be relatively thin. The electrodes 231b, 241b, and 251b are made of, for example, gold (Au) or indium (In).

Further, in each of the grating G0a, the grating G1a, and the grating G2a, the absorption members 235, 245, and 255 for adjusting the absorption of the incident X-ray or the modified amount of the phase are provided on the side of the grating detection portion 23, 24, and 25 (transmitted X-ray detection portion 1b side) opposite to the X-ray incident side (X-ray irradiation portion 1a side).

Effects of Fourth Embodiment

In the fourth embodiment, as described above, each of the semiconductor detection elements 231, 241, and 251, which are detection elements, is configured to include a semiconductor conversion film 231a, 241a, and 251a that converts an incident X-ray into a current and electrode 231b, 241b, and 251b that outputs the current signal converted by the semiconductor conversion film 231a, 241a, and 251a. With this, it becomes possible to easily detect an X-ray incident at the positions of the grating portions b3, b4, and b5 since an X-ray which is strong in permeability and difficult to directly detect can be converted to electrons (holes) by the semiconductor conversion film and a current signal generated by a voltage applied between each of the electrode 231b, 241b, and 251b and the electrode 232, 242, and 252) with the electrode 231b, 241b, and 251b and the electrode 232, 242, and 252 (the semiconductor detection element 231, 241 and 251).

Further, in the fourth embodiment, as described above, the material of the semiconductor conversion film 231a, 251a is made of a heavy element and the electrode 231b, 251b is formed to be thick to function as an absorption grating that absorbs the incident X ray so as not to transmit therethrough, thereby constituting the grating G0a and the grating G2a. The material of the semiconductor conversion film 241a is made of a light element and the electrode 241b is made to be thin so as to function as a phase grating for changing the phase of the incident X-ray, thereby constituting the grating G1a. With this, it is possible to easily constitute the absorption grating or the phase grating by merely changing the material of the semiconductor conversion film 231a, 241a, and 251a and the thicknesses of the electrode 231b, 241b, and 251b.

Other configurations and effects of the fourth embodiment are the same as those of the first embodiment.

Modified Embodiments

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

Figure 7:
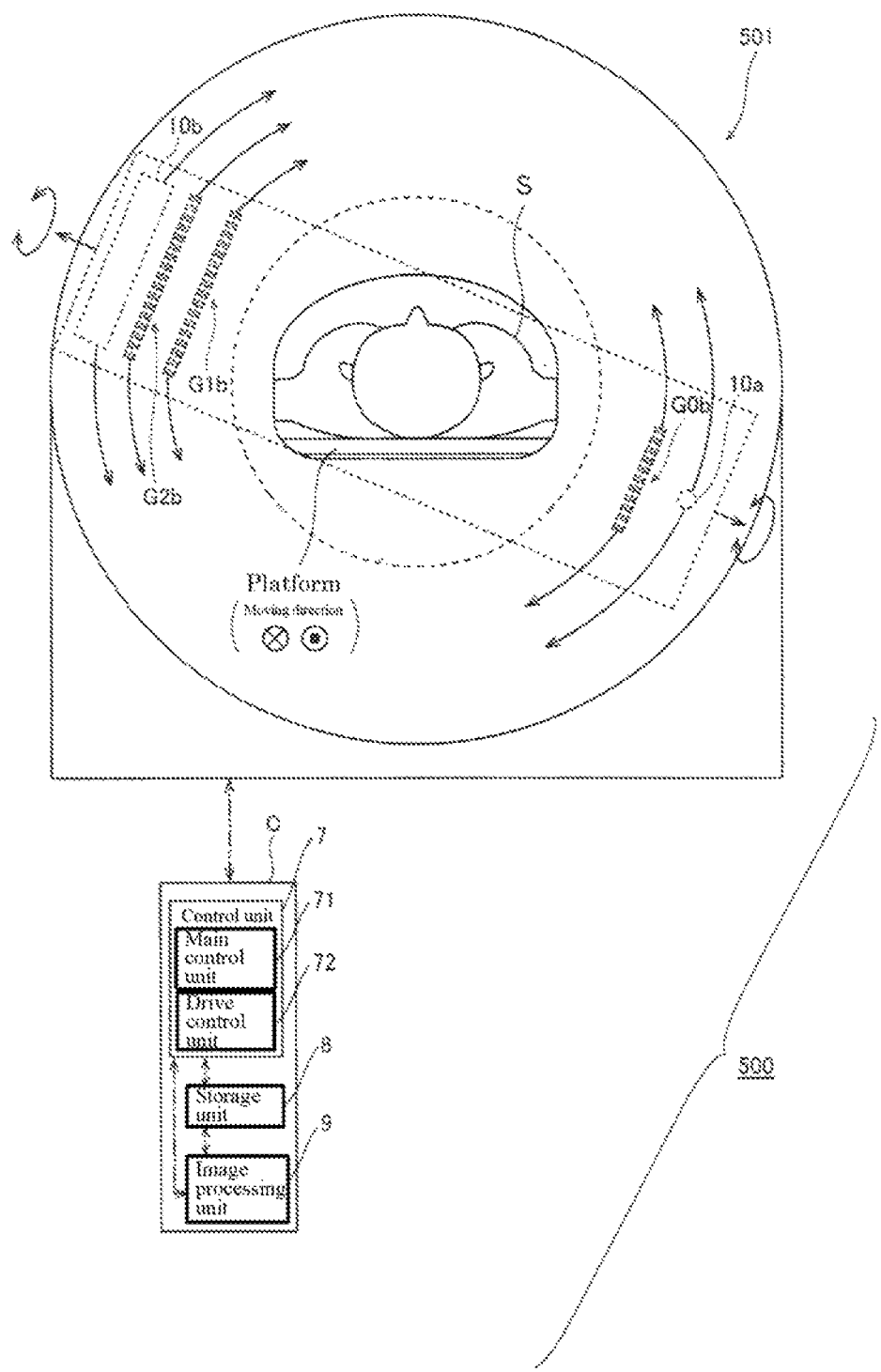
FIG. 7 is a diagram for explaining an example in which an X-ray inspection apparatus according to a modified example of the first to fourth embodiments of the present invention is used for a computer tomography apparatus.

For example, in the first to fourth embodiments, an example is shown in which the X-ray inspection apparatus 100 (200, 300, 400) is configured as an X-ray inspection apparatus 100 (200, 300, 400) which is fixed without moving with respect to the subject S at the time of image-capturing, but the present invention is not limited to this. In the present invention, as shown in the modified example of FIG. 7, the X-ray inspection apparatus 500 may be configured to include a computer tomography apparatus 501 for capturing an X-ray image of the subject S by rotating each of the X-ray irradiation portion 10a, the grating G0b (first grating), the grating G1b (second grating), the grating G2b (third grating), and transmitted X-ray detection portion 10b at the time of image-capturing around the subject S.

With this configuration, it is possible to configure a computer tomography apparatus 501 capable of suppressing the excessive exposure of the subject S and the increase in image-capturing time due to the absorption by each of the grating (grating G0b, grating G1b, and grating G2b) of the X ray irradiated from the X-ray irradiation portion 10a. With this computer tomography apparatus 501, by acquiring a plurality of X-ray images (the absorption image, the phase image, and the dark field image) while rotating with respect to the grating detection portion of the subject S and combining them, the tomographic image of the absorption image, the phase image, and the dark field image of the subject S can be obtained, respectively.

It should be noted that the term "at the time of image-capturing" means the moment when an X-ray is actually irradiated and image-capturing is performed, and does not include the time between image-capturing in which the movement, etc., of the grating is performed due to fringe scanning or the like. Further, the subject S is not limited to a human body.

In the first to fourth embodiments, it is configured such that one scintillator corresponds to each photoelectric conversion element, but the present invention is not limited to this. In the present invention, a scintillator may be arranged as indicated by the radiation detector Ga, Gb, Gc, and Gd (which is composed of either the first grating, the second grating, or the third grating) of FIGS. 8A to 8H. Specifically, as shown in FIGS. 8A and 8B and FIGS. 8C and 8D, it may be configured by the scintillator 21a (21b) connected in the line direction (Y direction). At this time, as shown in FIG. 8B, it may be configured such that the pitch of the photoelectric conversion element 22a in the line direction perpendicular to the line and a direction perpendicular to the line is equal.

Further, as shown in FIG. 8D, in order to suppress the missing of the photon converted in the scintillator 21b, it may be configured such that the pitch of the photoelectric conversion element 22b in the line direction (Y direction) is set to be narrow (packed) with respect to the pitch in a direction (X direction) orthogonal to the line.

Further, as shown in FIGS. 8E and 8F and FIGS. 8G and 8H, it may be configured to arrange a pair of a scintillator 21c (21d) and a photoelectric conversion element 22c (22d) in a matrix form having a periodic structure of the opening portion and the non-opening portion in two directions or in a staggered pattern. At this time, since the pair of the scintillator 21c (21d) and the photoelectric conversion element 22c (22d) is arranged so as to have a periodic structure with respect to the two directions, it is possible to detect the deviation of the phase of the X-ray with respect to the two directions perpendicular to the direction in which the periodic structure appears and the scattering of the X-ray.

Similarly, a semiconductor detection element which is a pair of a semiconductor conversion film and an electrode may be arranged so as to have a periodic structure in two directions.

In addition, in the first to fourth embodiments, although an example is shown in which each grating (first grating, second grating, third grating: radiation grating detector) is used in a state of being incorporated in an X-ray inspection apparatus, but the present invention is not limited thereto. In the present invention, each grating may be removed from the X-ray inspection apparatus and used as a radiation grating detector. At that time, in each grating (radiation grating detector), radiation other than X-rays such as gamma rays may be image-captured.

In the first to fourth embodiments described above, the subject is placed on the X-ray irradiation portion side with respect to the second grating. However, the subject may be placed on the transmitted X-ray detection portion side with respect to the second grating.

Also, in the first to fourth embodiments, an example is shown in which the absorption member is provided in each grating (the first grating, the second grating, and the third grating) is shown, but the absorption member may not be provided.

In the first to fourth embodiments, the readout circuit is integrated with each grating (the first grating, the second grating, and the third grating). However, the readout circuit may be configured separately from each of the gratings.

In the first to fourth embodiments, the width of the grating portion in a direction intersecting with the direction of the line-shaped arrangement is set to ½ of the pitch. However, it may be ¼ or more and ¾ or less of the pitch.

Further, in the first to fourth embodiments, an example is shown in which the second grating is configured to function as a phase grating. However, the second grating may be configured to function as an absorption grating.

Further, in the first to third embodiments, an example is shown in which each of the second grating and the third grating is provided with a removable transparent substrate together with a scintillator. However, it may be configured such that without providing a transparent substrate to the second grating and third grating, a scintillator is directly provided on the element substrate.

Further, in the second embodiment, it is configured such that when the radiation (X-ray) corresponding to the energy lower than the threshold value is incident by the discriminator, the second signal is output and the low energy X-ray image (lower than the threshold value) is acquired. However, the present invention is not limited thereto. Further, in the present invention, it may be configured such that when the radiation (X-ray) corresponding to the energy higher than the threshold value is incident by the discriminator, the second signal is output and the high energy X-ray image (higher than the threshold value) is acquired. However, the present invention is not limited thereto.

Further, it also may be configured such that two or more pairs of a discriminator and a counter (photon number counting portion) are provided for one grating detection portion, and in one grating detection portion, the number of photons corresponding to different energies discriminated by two or more discriminators may be counted by a counter to acquire two or more X-ray images at the same time.

The invention claimed is:

1. An X-ray inspection apparatus comprising:
an X-ray irradiation portion configured to irradiate an X-ray to a subject;
a first grating configured to generate a grating image of the incident X-ray, and a second grating configured to absorb the X-ray at a position where the grating image is generated to shield the X-ray; and
a transmitted X-ray detection portion configured to detect the X-ray transmitted through the subject, the first grating, and the second grating,
wherein the first grating and the second grating include an opening portion through ehich the radiation transmits and a grating portion forming a non-opening portion adjacent to an opening portion, and
wherein the grating portion of the first grating includes a first grating detection portion to detect the incident X-ray transmitted through the grating portion of the first grating portion.

2. The radiation grating detector as recited in claim 1, wherein at least one of the first grating detection portion and the second grating detection portion includes a plurality of detection elements which corresponds to each pixel and directly or indirectly detects the radiation incident on the non-opening portion to output an electric signal.

3. The radiation grating detector as recited in claim 2, wherein at least one of the first grating detection portion and the second grating detection portion further includes a scintillator that converts the incident radiation into light having a frequency lower than a frequency of the radiation, and the detection element is configured by a photoelectric conversion element that detects the light having a low frequency converted by the scintillator and outputs an electric signal.

4. The radiation grating detector as recited in claim 3, wherein the grating portion functions as an absorption grating that absorbs the incident radiation to prevent transmission of the incident radiation to configure the first grating or the second grating when a thickness of the scintillator in an incident direction of the radiation is larger than the case where the grating portion functions as a phase grating that changes a phase of the incident radiation, and functions as the phase grating to configure the first grating when the thickness of the scintillator in the incident direction of the radiation is smaller than the case where the grating portion functions as the absorption grating.

5. The radiation grating detector as recited in claim 3, further comprising:
a transparent substrate provided with the scintillator and configured to allow transmission of the radiation,
wherein the transparent substrate is detachably attached to one of element substrates together with the scintillator, the one of element substrates being provided with the photoelectric conversion element.

6. The radiation grating detector as recited in claim 2, wherein the detection element is composed of a semiconductor detection element including a semiconductor conversion film that converts the incident radiation into an electric current and an electrode that outputs a current signal converted by the semiconductor conversion film.

7. The radiation grating detector as recited in claim 6, wherein the grating portion functions as an absorption grating that absorbs the incident radiation to prevent transmission of the radiation to configure the first grating or the second grating when the semiconductor conversion film is heavier than the case where the grating portion functions as a phase grating that changes a phase of the incident radiation or the electrode is thicker than the case where the grating portion functions as the phase grating, and
the grating portion functions as a phase grating that changes a phase of the incident radiation to configure the first grating when the semiconductor conversion film is lighter than the case where the grating portion functions as the absorption grating or the electrode is thinner than the case where the grating portion functions as the absorption grating.

8. The X-ray inspection apparatus as recited in claim 1, wherein the grating portion of the second grating includes a second grating detection portion to detect the incident X-ray transmitted through the grating portion of the second grating portion.

9. The X-ray inspection apparatus as recited in claim 8, wherein a temporal fluctuation of intensity of the X-ray irradiated by the X-ray irradiation portion and detected by at least one of the first grating detection portion and the second grating detection portion is obtained, and a correction is made so that luminance of an X-ray image acquired at different times becomes constant based on the obtained temporal fluctuation of the intensity.

10. The X-ray inspection apparatus as recited in claim 8, wherein the first grating and the second grating are configured to be movable relative to each other, and wherein X-ray inspection apparatus is configured to acquire a positional fluctuation of at least one of the first grating and the second grating based on a change of intensity of the X-ray transmitted through the subject detected by at least one of the first grating detection portion and the second grating detection portion and configured to relatively move the first grating, the second grating, and the third grating to correct the positional fluctuation.

11. The X-ray inspection apparatus as recited in claim 8, wherein X-ray inspection apparatus is configured to acquire an X-ray image in which resolution is complimented based on a combination of at least two or more X-ray images different in resolution among a first X-ray image captured by the grating detection portion a second X-ray image captured by the second grating detection portion, and a third X-ray image captured by the transmitted X-ray detection portion.

12. The X-ray inspection apparatus as recited in claim 8, wherein the X-ray inspection apparatus is configured to acquire an X-ray image in which a composition of the subject is reflected based on a combination of at least two or more X-ray images captured by X-rays different in energy among a first X-ray image captured by the first grating detection portion, a second X-ray image captured by the second grating detection portion, and a third X-ray image captured by the transmitted X-ray detection portion.

13. The X-ray inspection apparatus as recited in claim 12, wherein at least one of the first grating detection portion and the second grating detection portion includes:
 a scintillator configured to convert the incident X-ray into light having a frequency lower than a frequency of the X-ray;
 a plurality of photoelectric conversion elements corresponding to each pixel and configured to detect a plurality of photons included in the light converted by the scintillator and output a first signal;
 a discriminator configured to discriminate the first signal by at least one threshold value for discriminating whether or not an energy value of the photons indicated by the first signal falls within a range of a predetermined energy value and output a second signal corresponding to the first signal when the energy value of the photons indicated by the first signal falls within the range of the predetermined energy value; and
 a photon number counting portion configured to count the number of the photons corresponding to the range of the predetermined energy value based on the second signal output based on the first signal discriminated by the threshold value the discriminator.

* * * * *